United States Patent [19]
Gormley et al.

[11] Patent Number: 5,844,406
[45] Date of Patent: Dec. 1, 1998

[54] METHOD AND APPARATUS FOR TESTING AND MEASURING FOR POROSITY AND ANOMALIES OF MATERIALS USING ELECTRON BEAMS

[76] Inventors: Gregory J. Gormley; Robert Griebel, both of 85 Justice Dr., Newtown, Pa. 18940

[21] Appl. No.: 699,050

[22] Filed: Aug. 21, 1996

Related U.S. Application Data

[60] Provisional application No. 60/002,693, Aug. 23, 1995.

[51] Int. Cl.⁶ ................................................. G01R 27/26
[52] U.S. Cl. .......................................... 324/71.3; 324/557
[58] Field of Search .................................. 324/555, 556, 324/557, 559, 452, 455, 456

[56] References Cited

U.S. PATENT DOCUMENTS

| | | |
|---|---|---|
| 2,221,323 | 11/1940 | Gammeter . |
| 2,320,516 | 6/1943 | Gammeter . |
| 2,622,129 | 12/1952 | Killian ..................................... 324/557 |
| 2,649,960 | 8/1953 | Gammeter . |
| 3,339,136 | 8/1967 | Rasor ....................................... 324/557 |
| 4,443,764 | 4/1984 | Suh et al. . |
| 4,583,039 | 4/1986 | Kolcio et al. . |
| 4,620,145 | 10/1986 | Dietz et al. . |
| 4,791,811 | 12/1988 | Barbee ..................................... 324/557 |
| 4,914,395 | 4/1990 | Hamada . |
| 4,947,470 | 8/1990 | Darilek .................................... 324/557 |
| 5,050,426 | 9/1991 | Torres-Ibanez . |
| 5,097,214 | 3/1992 | Schinhärl . |
| 5,196,799 | 3/1993 | Beard ....................................... 324/557 |
| 5,455,507 | 10/1995 | Horenstein . |
| 5,543,719 | 8/1996 | Lomasney . |

FOREIGN PATENT DOCUMENTS

| | | |
|---|---|---|
| 1 055 847 | 12/1955 | Germany . |
| 1 169 159 | 6/1958 | Germany . |
| 2 040 757 | 2/1972 | Germany . |
| 2257649 | 11/1972 | Germany ................................ 324/557 |
| 32 23 664 | 12/1983 | Germany . |
| 39 15797 | 11/1989 | Germany . |
| 41 05 135 | 8/1992 | Germany . |
| 41 27 740 | 3/1993 | Germany . |
| 44 26 225 | 1/1996 | Germany . |
| 0201077 | 11/1983 | Japan ...................................... 324/557 |
| 1 323 567 | 7/1973 | United Kingdom . |
| 91/10889 | 7/1991 | WIPO . |
| 96/03635 | 2/1996 | WIPO . |

OTHER PUBLICATIONS

J. Iovine, "Corona formation in Kirlian photography", *Kirlian Photography—A Hands-On Guide*, pp. 18–20, TAB Books, 1994.

A.D. Moore, *Electrostatics*, pp. 63–65, 73–74, Doubleday & Company, Inc., 1968.

J.J. Thomson, *The Discharge of Electricity Through Gases*, Charles Scribner's Sons, 1898.

*Primary Examiner*—Maura K. Regan
*Attorney, Agent, or Firm*—Ratner & Prestia

[57] ABSTRACT

The porosity and integrity of a nonconductive material is determined using electron beams and electronic instrumentation. The electric corona discharge from holes in the nonconductive material is detected and analyzed in order to determine the presence of viral and sub-viral sized voids or holes, as well as other material anomalies such as blisters and bubbles.

50 Claims, 19 Drawing Sheets

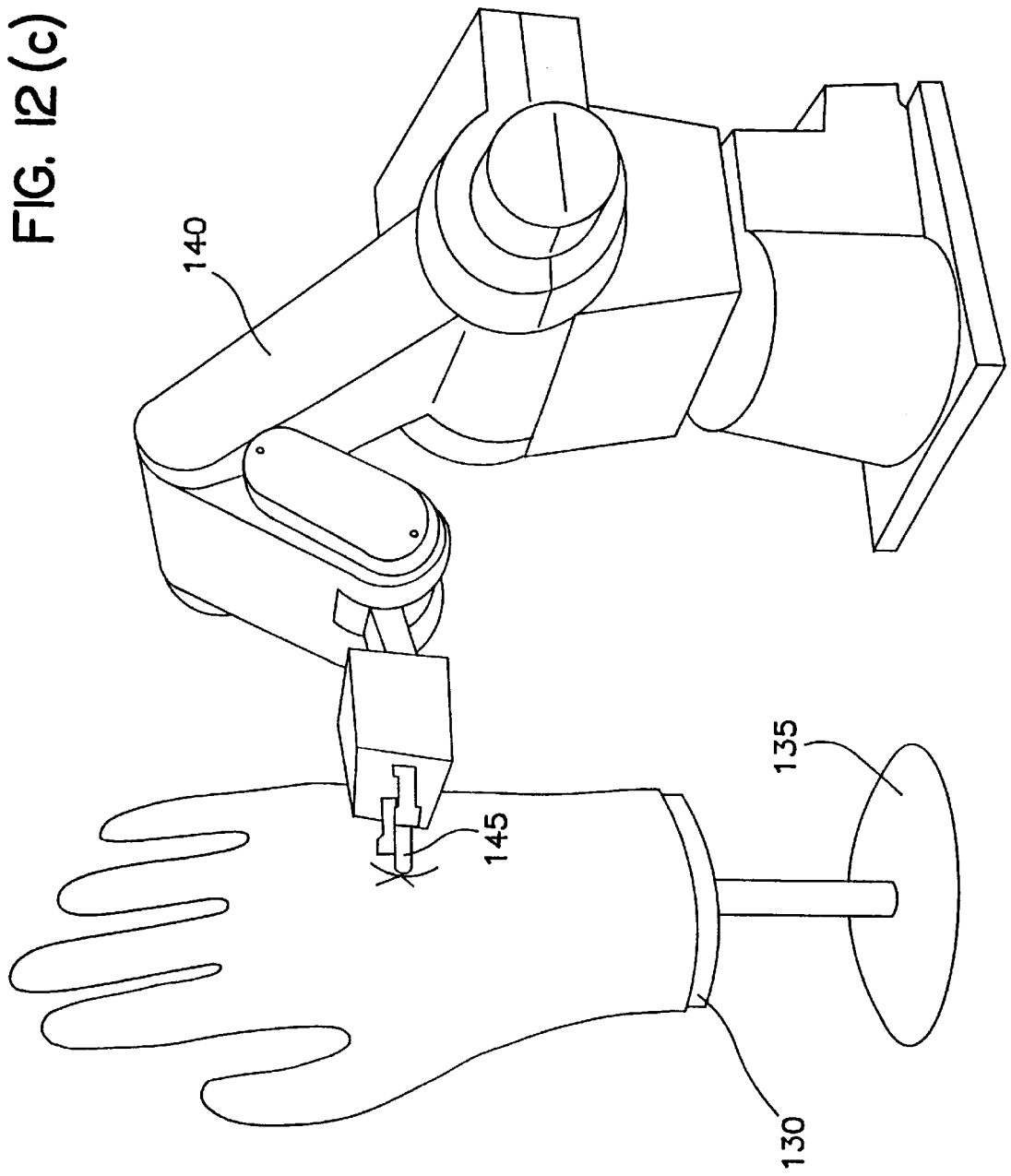

METHOD AND APPARATUS FOR TESTING AND MEASURING FOR POROSITY AND ANOMALIES OF MATERIALS USING ELECTRON BEAMS

This application claims the benefit of U.S. Provisional application Ser. No. 60/002,693 filed Aug. 23, 1995.

FIELD OF THE INVENTION

This invention relates to a method and apparatus for the on-line, real-time, non-destructive porosity and anomaly testing and measuring of nonconductive materials, including a protective barrier material, such as a condom, a glove, encapsulation, packaging, or filtration media for the detection of viral and sub-viral sized apertures, voids, holes, blisters, contaminants, stress fractures, overlapped material, formulation defects and other anomalies, and more particularly to an electronic measuring method and apparatus which utilizes electron beams and electronic instrumentation to measure electronic corona discharge from the holes and anomalies in the nonconductive material.

BACKGROUND OF THE INVENTION

There is much concern among world health organizations and regulatory agencies regarding the quality of nonconductive materials, including protective barrier materials or products, such as condoms or gloves. The concern is due to the fact that disease-causing viruses such as the AIDS virus and the hepatitis B virus can pass through small holes or voids present in these materials or goods, thus infecting the user with the virus. These holes or voids may be formed during the manufacturing of the nonconductive materials or pursuant to anomalies present in the nonconductive materials. Accordingly, the present invention has been developed for the testing and measuring of the porosity and anomalies of these nonconductive materials. In particular, the present invention has been developed for the on-line, real-time, non-destructive, non-contact, non-abrasive, dry testing and measuring of nonconductive materials, including thin film protective barrier materials, for voids, holes, or anomalies having a diameter of as little as one nanometer. Moreover, the present invention can detect anomalies in the material such as contamination, blisters, bubbles, uncatalyzed or unblended resin, low density material (e.g., weak molecular crosslinking strength), high density material, overlapping material, stress fractures, formulation defects, and other structural and non-void anomalies in the material.

Products and materials used to screen viral-size viruses must have their porosity and anomaly presence determined in order to insure that no holes are present or may be formed by anomalies which would permit the passage of a virus. These viruses may be as small as twenty nanometers in diameter. Goods and materials that may act as viral barriers include condoms, medical grade gloves, thin film membranes, filtration media, materials used in electronic applications, gowns and aprons used in the medical field and operating room environments. Goods and materials that may act as filter media include medical and scientific membranes, fiber and cloth-like filled devices, and microporous analytical and diagnostic membranes, as well as various polymer combinations.

One primary test for determining the porosity of nonconductive thin film materials is the water or electrical hydraulic test. Using this test, the product or material to be tested, such as a condom, is placed on a tube-shaped electrode or mandrel and is submersed in a water bath or electrolyte solution. An electrical potential is applied between the mandrel and the water solution. If there is a void of material in the condom, the water will pass from the charged container water bath to the electrode, causing a short circuit. A current reading will be displayed on a connected ammeter indicating that a defective void exists in the material, and this material is rejected. However, this test can only determine if there is a sizable hole in the material. It cannot reveal the presence of an anomaly, such as a blister or a bubble, in the material because the blister or the bubble will not break in the water test, thus not permitting the water to pass from the water bath to the ground However, a blister or bubble could very easily break in the use of the condom and thus the condom would fail during use. Therefore, this test would not find the defect in the condom. Another drawback of the water test is that only holes of about fifty microns or greater will be detected, due to the surface tension of the water. It has been proposed to add soap or alcohol to the water in order to decrease the surface tension. However, even with a lower surface tension, this test will not detect viral size holes.

A second primary test which is used to determine the porosity of materials is called a dry test or a spark test. This method involves an electrically charged brush, charged with 1300 to 1500 volts A.C., 60 Hz. The brush is conductive and it brushes against the mandrel which the material (e.g., the condom) is placed on. Both the brush and the mandrel rotate. When there is a large void, about 50 to 100 microns, the voltage from the brush will spark through as a straight forward, very thick spark. Because it is a strong discharge, it creates large holes. This method is destructive because the brush touches and breaks the condom. Furthermore, a very strong current flows which can destroy the condom.

A third test is disclosed in U.S. Pat. No. 5,196,799 entitled METHOD AND APPARATUS FOR TESTING A PROTECTIVE BARRIER MATERIAL FOR PINHOLES AND TEAR STRENGTH and issued to Beard et al. This test is basically a water test that is conducted at different frequencies, not just D.C. or 60 Hz. This method permits the discovery of holes, bubbles and blisters in the material being tested. This is a capacitive test in which distance, environment and thickness of the product are critical to the repeatability and calibration of the test It is an integral measurement, meaning it measures relatively large areas as one "gray" measurement. It is also a wet tester. One of the inherent problems with wet testing is that after the material has been wet then it must be dried, and usually dried with hot air. The hot air, containing ozone, weakens the latex material and thus increases or enhances the number of voids that might be present in the final product.

In addition, the above tests are used in conjunction with more extensive destructive test methods to statistically sample lots of the finished product. Laboratory testing has shown that in a given finished production lot, some products have small and large holes, while in another given lot, there may be few, if any, defective product. Thus, more accurate and reliable process testing of each manufactured product is needed.

The foregoing illustrates the limitations known to exist in present porosity testing methods and apparatuses. Thus, it is apparent that it would be advantageous to provide an alternative porosity testing method and apparatus s which will non-destructively detect viral size voids, blisters, bubbles, and other anomalies on the production line in fluctuating environments and in real-time for nonconductive materials.

SUMMARY OF THE INVENTION

The present invention provides a method and apparatus of non-destructive testing using a corona beam and the Griebel- Gormley Aperture Effect. Viral and subviral apertures or voids of material, as well as anomalies such as bubbles and blisters, are detected in the present invention through the use of a corona beam.

Corona beam formation is disclosed in a text by Iovine, "Kirlian Photography" (TAB Books, 1994), which is incorporated herein by reference.

The problems of the prior art are overcome by the present invention. These problems include the operation of the brush in the dry test and the necessity of drying the material in the wet test. Furthermore, subviral size and viral size holes can be found down to about 1 to 10 nanometers, as opposed to the prior art which detects holes only as small as about 50 microns. Finally, the present invention can detect bubbles and blisters and other abnormalities and anomalies in the material. This testing is performed dry, absolutely non-destructively in real-time, on-line, in fluctuating environments, with non-contact.

BRIEF DESCRIPTION OF THE DRAWINGS

FIG. 12(c) is a further exemplary embodiment, using an articulating robotic arm, to determine the porosity of a nonconductive barrier glove in accordance with the present invention.

DESCRIPTION OF PREFERRED EMBODIMENTS

Figure 1A:
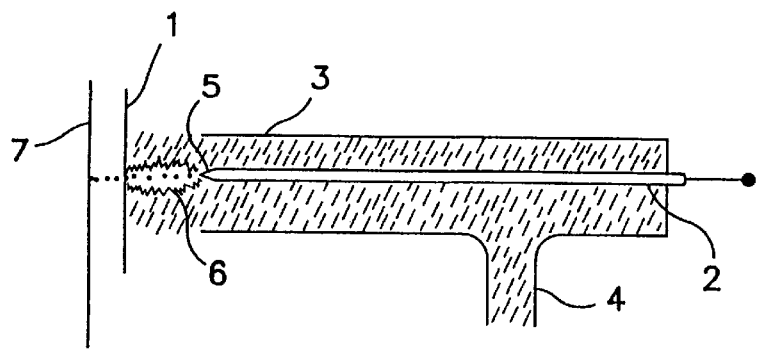
FIG. 1(a) is a schematic representation of the Griebel-Gormley Aperture Effect in conjunction with a small void, hole or anomaly in the testing material.

In general terms, the porosity or presence of anomalies of a nonconductive material is determined by using an electron sensor in an open atmosphere under a fluid cover gas, or a flow of a cover gas. The cover gas is directed on the material and, if there is a small aperture, hole or anomaly in the material, a change in the electric discharge or "corona" (also known as an electron beam, an electrostatic corona or a corona discharge) occurs, which is measured by the sensor. The electron sensor comprises an electrode and a sensing mechanism which records electrons that are sent through the hole or anomaly in the nonconductive material. The occurrence of this change in discharge is due to the below-described Griebel-Gormley Aperture Effect (sometimes referred to herein as "the Aperture Effect").

It should be noted that anomalies in the material include, but are not limited to, contamination, blisters, bubbles, uncatalyzed or unblended resin, low density material (e.g., weak molecular crosslinking strength), high density material, overlapping material, stress fractures, formulation defects, and other structural and non-void anomalies in the material.

It should be noted that the diameter of the anode tip in the electron sensor, the quality of the plating material (e.g., barium, platinum, gold, silver), and the heating of the anode and cathode tips are factors that relate to the quality and length of the electric discharge (i.e., the corona beam) that is detected. Other important factors are the dielectric quality of the material being tested, the type of defect that is being detected, and the operating parameters of the testing equipment, such as the frequency, the amplitude, the wave-shape and the voltage. The proper combination of these factors leads to the ability to detect subnanometer size apertures, holes or anomalies in the material being tested.

The Griebel-Gormley Aperture Effect is based on the point-to-point effect, a known effect, which is described in a text by Moore, "Electrostatics" (Doubleday & Company, Inc., 1968), which is incorporated herein by reference. The Griebel-Gormley Aperture Effect is shown by the use of a smooth, rounded grounded cathode (i.e., approximately cylindrical) in proximity to a tip of an anode (a point). Very few electrons (or corona) are discharged if the voltage is low enough. But when the cathode is masked with a dielectric material containing a very small void of material (or hole or anomaly), an electrical point is masked out on the grounded cathode. A point-to-point effect would be created and electrons would flow from the cathode through the hole or anomaly in the dielectric material to the anode tip without increasing the applied voltage. This flow of electrons is detected as a change in the electric discharge.

A cover gas is also important in achieving the Griebel-Gormley Aperture Effect. Typical cover gases include nitrogen, noncombustible gases, noble gases, and dehydrated air. The results vary with the particular cover gas used. It makes a dramatic difference whether nitrogen is used as opposed to air or neon or other noble gases. The flow rate and gas pressure are also important factors; the higher the gas pressure, the more gas flows and the beam lengthens. As the pressure increases, the gas becomes more dense, and the electrons flowing from the cathode to the anode become slower moving. For example, with a pressure of about 1 atmosphere in a cover gas of air, the electrons will move at about 1/10 the speed of light. If the pressure is increased, the speed will decrease.

It should also be noted that the beam may move and wander in the cover gas environment. The beam is self-seeking within the focus of the fluid cover gas. Thus, the beam moves in the area of the material bounded by the fluid cover gas in order to locate a properly sized aperture or anomaly.

It should also be noted that the sensor may be positioned using an automatic positioning device such as a servo motor, a stepper motor or a programmable positioning robot.

Other important factors in the creation of the Griebel-Gormley Aperture Effect are the supply voltage, the frequency of the pulsed D.C., and the distance from the cathode to the anode. Moreover, the distance between the cathode and the material being tested is an important factor in obtaining the Aperture Effect. If the material being tested is too far from the cathode, the Aperture Effect will be lost.

Referring to FIG. 1(a), there is shown a nonconductive material 1 which is being tested for a hole, an aperture or an anomaly. This material 1 may be, for example, a piece of latex used in condoms or medical grade gloves. A very small hole, on the order of 200 nanometers, is shown in the center of the material 1. It should be noted that the following analysis is also applicable for the testing of a material for the presence of an anomaly instead of a hole. Electrons flow from the ground 7 (the cathode) towards the anode 2 as a corona beam 6. This corona beam 6 is formed because of the small aperture in the material 1. The ground 7 may be a smooth, rounded material or model, such as a metallic object (e.g., a plate or a roller) or a metal mandrel. Normally, a negligible amount of electric discharge would flow from the ground 7. However, the point 5, which is at the tip of the anode 2, responds to the aperture in the material 1 as if the aperture were another point. This in turn gives rise to a point-to-point effect. When there is a point-to-point contact present, an increase in the corona discharge flow occurs. We call this effect the Griebel-Gormley Aperture Effect. Due to the presence of a very small void, or anomaly, a strong field of electrons is generated. This does not occur when a point comes in contact with a smooth, rounded conductive model, such as the metal mandrel, plate or roller.

A fluid cover gas 4 is directed to flow through a housing 3 which encases the anode 2 and to flow toward a surface of the nonconductive material. This cover gas 4 amplifies the Griebel-Gormley Aperture Effect by eliminating the ambient electron flow and attenuating the beam. The cover gas 4 may be nitrogen, a noncombustible gas, or a noble gas such as xenon, krypton, neon, and argon. The cover gas 4 may also be dehydrated air which works well for certain materials. The air is dehydrated to eliminate the presence of any humidity fluctuations.

Figure 1B:
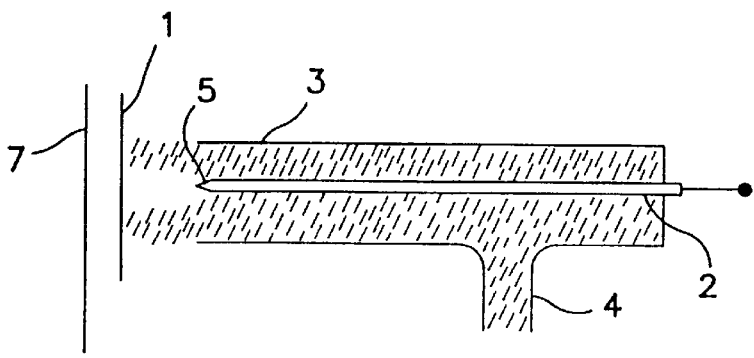
FIG. 1(b) is a schematic representation of the Griebel-Gormley Aperture Effect in conjunction with no void, hole or anomaly in the testing material.
Figure 1C:
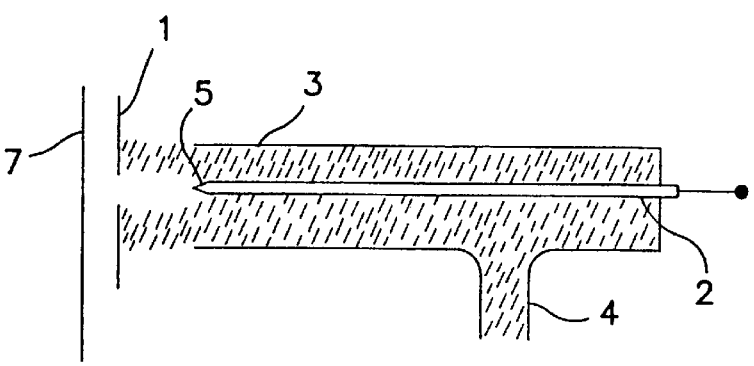
FIG. 1(c) is a schematic representation of the Griebel-Gormley Aperture Effect in conjunction with a large void, hole or anomaly in the testing material.
Figure 1D:
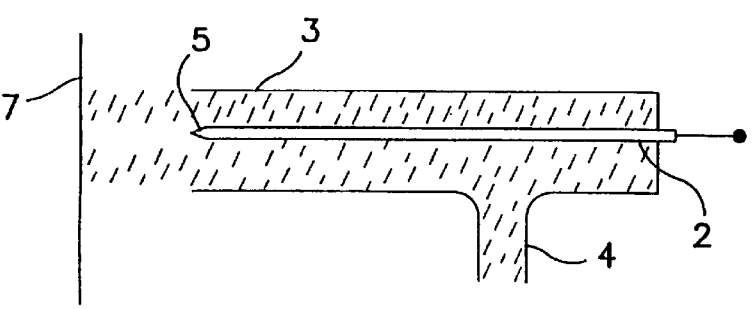
FIG. 1(d) is a schematic representation of the Griebel-Gormley Aperture Effect in conjunction with no testing material.

FIGS. 1(b)–1(d) contain similar elements as have been described above with respect to FIG. 1(a). These elements are labeled identically and their description is omitted for brevity.

Referring to FIG. 1(b), there is shown the same elements of FIG. 1(a) except the material 1 has no hole or aperture in it. The material 1 is a good dielectric material (an insulator) that prevents electrons from flowing. Thus, there is a negligible flow of electrons from the ground 7. As a result, there is no Griebel-Gormley Aperture Effect because there is only one point (the point 5) and thus no point-to-point effect may occur.

Referring to FIG. 1(c), there is shown the material 1 with a very large void in it. This void may be from 2 millimeters to 10 millimeters in diameter. Due to the size of the void, there is no point-to-point effect present because the material 1 does not create a small enough window to cover up the ground 7 (the cathode) in order to create a point cathode. Thus, there is no measurable change in the flow of electrons from the ground 7.

Thus, based on FIGS. 1(a) and 1(c), an inverse relationship exists between the strength of the electric discharge and the size of the void of the nonconductive material. As the void size increases, the strength of the electric discharge decreases.

Referring to FIG. 1(d), no dielectric material 1 is present. Thus, because the ground 7 is smooth and rounded, no point-to-point effect is present between the ground 7 and the tip 5 of the anode 2. There is a negligible flow of electrons.

Figure 2:
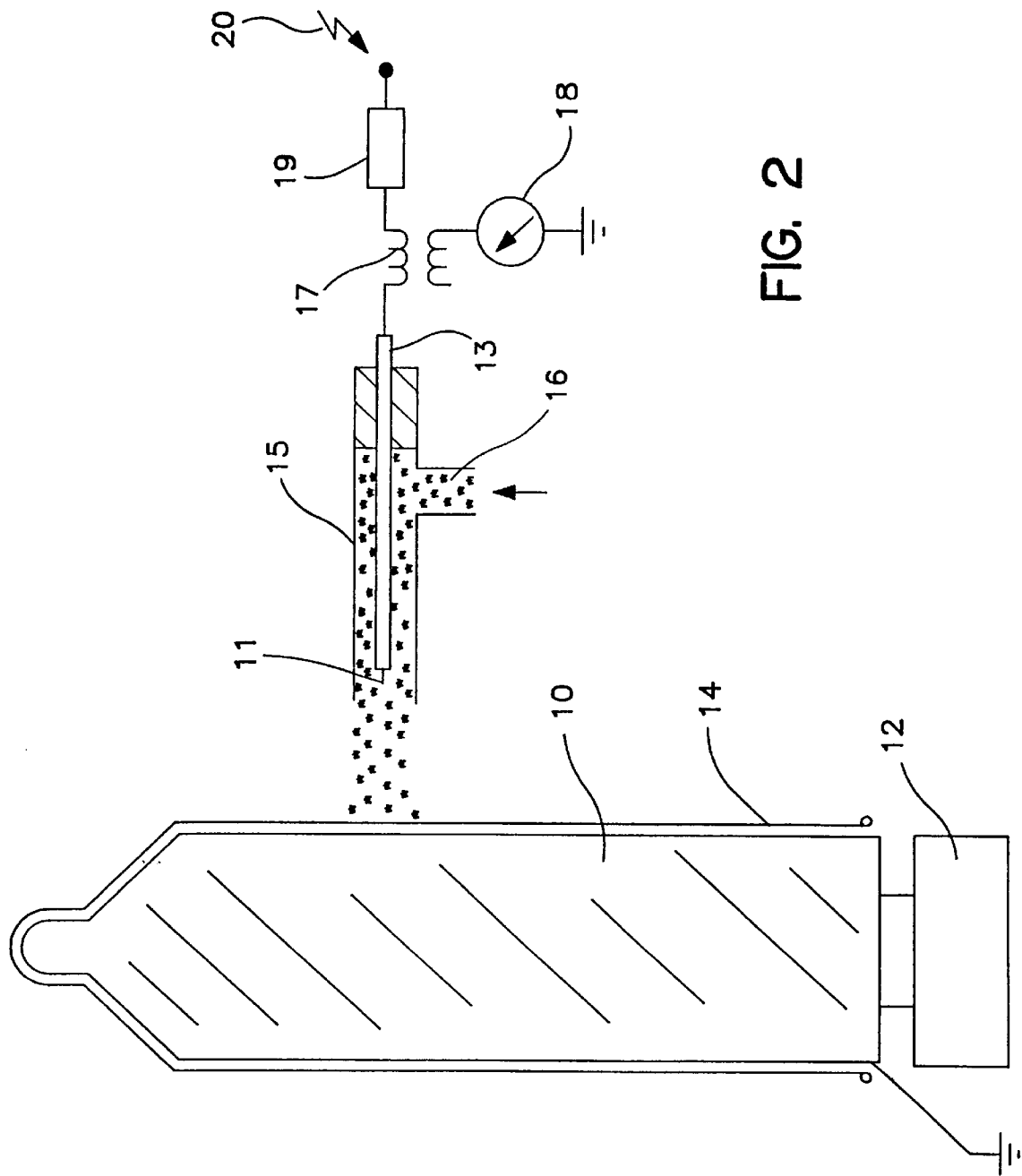
FIG. 2 is an exemplary circuit for determining the porosity of a condom in accordance FIG. 1(b).

Referring to FIG. 2, there is shown a condom 14 placed on a mandrel 10 which acts as the grounded cathode. The porosity of the condom is to be determined. The mandrel 10 is mounted on an automatic positioning device such as a robot, a stepper motor or servo motor 12 which spins the mandrel 10.

The housing 15 contains the fluid cover gas 16 as its flow is directed over any electron beam. The tip 11 of the anode 13 attracts electrons. However, in this exemplary circuit, a negligible amount of electrons are flowing because the condom does not contain a small void. There is no Griebel-Gormley Aperture Effect. This is similar to the situation described above with respect to FIG. 1(b). Note that the housing 15 has an inner diameter of about 4 mm and the anode 13 has a diameter of about 1 mm.

The electronic measurement instrumentation and circuitry is as follows. The anode 13 is connected to a coil 17. An ammeter 18 measures the flow of current in the coil 17. A large resistor 19 and a high voltage pulsed DC power supply 20 are connected in series to the coil 17. This circuitry is desirable to detect a hole in the material being tested. Other electronic measurement instrumentation and circuitry, discussed in detail below with respect to FIG. 13, is preferred to detect the presence of an anomaly. The circuitry of FIG. 13 is preferably adapted for use in FIGS. 2–12(c) to test for the presence of anomalies rather than holes.

Figure 3:
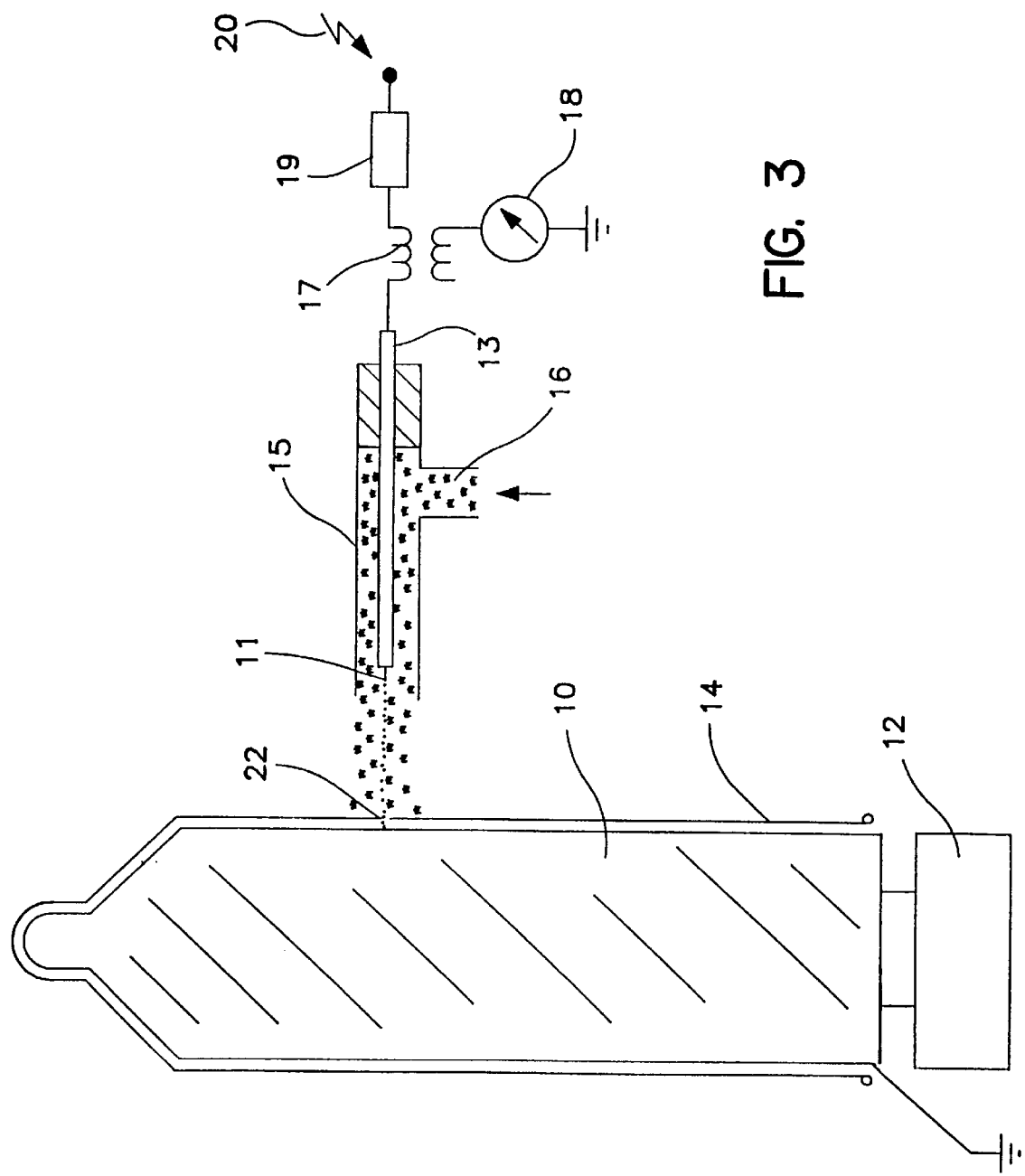
FIG. 3 is an exemplary circuit for determining the porosity of a condom in accordance FIG. 1(a).
Figure 4:
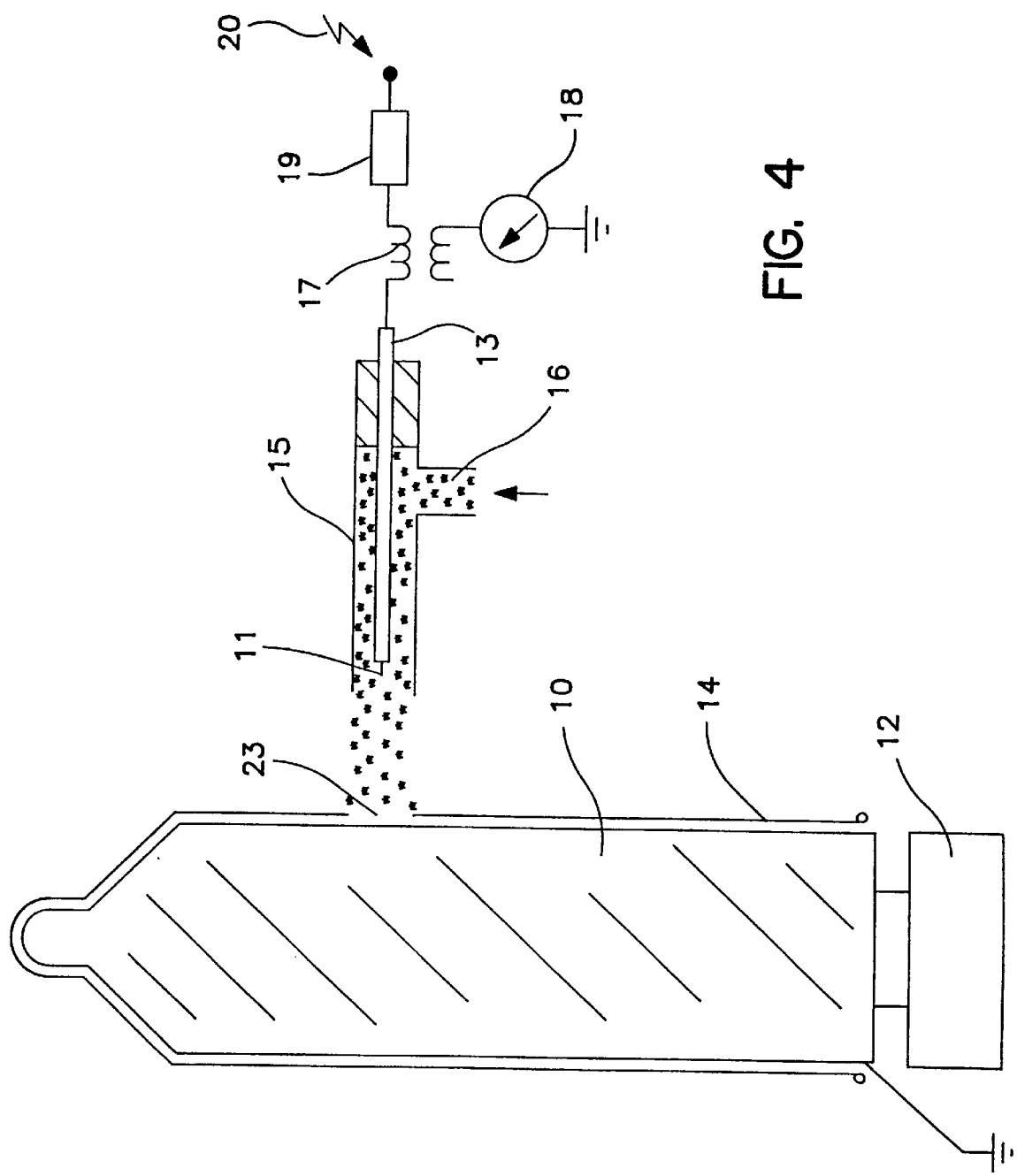
FIG. 4 is an exemplary circuit for determining the porosity of a condom in accordance FIG. 1(c).

FIG. 3 and FIG. 4 contain similar elements as have been described above with respect to FIG. 2. These elements are labeled identically and their description is omitted for brevity.

Referring to FIG. 3, there is shown a similar exemplary circuit as shown in FIG. 2, except that the condom 14 has a very small hole 22 in it. This small hole 22 would create the Griebel-Gormley Aperture Effect because a point-to-point situation would be formed. This would create an increase in the flow of electrons from the mandrel 10 (the grounded cathode) to the tip 11 of the anode 13. The increased electron flow would be detected by the coil 17 and displayed on the ammeter 18. The cover gas 16 assists the electron beam in being conveyed from the mandrel 10 to the anode 13. Here, a desirable cover gas is dehydrated nitrogen gas, a very consistent gas that does not require recalibration each time it is used. Furthermore, nitrogen gas has the advantage of not creating any ozone, which may be created by the corona discharge in an oxygen atmosphere to affect the condom 14 which may be harmed if made of latex.

Referring to FIG. 4, there is shown a similar exemplary circuit as shown in FIG. 2, except that the condom 14 has a very large void 23 in it. The void 23 is so large that a point-to-point effect may not be created. Thus, the Griebel-Gormley Aperture Effect disappears. The voltage, or potential, applied to anode 13 is not sufficient to draw an appreciable amount of electrons out of the grounded cathode mandrel 10. As a result, there is a negligible electron flow from the mandrel 10 to the tip 11 of the anode 13. The ammeter 18 would not produce an output because the coil 17 would not detect any current.

The size of the void 23 relative to the size of the tip 11 of the anode 13 is critical. If, for example, the anode tip 11 is 3000 times smaller than the size of the hole 23, the Aperture Effect will not be obtained. The achievement of the Aperture Effect is dependent, among other factors, such as frequency, amplitude and waveshape, described above, on the relative sizes of the void 23 and the anode tip 11 diameter. If that relation is not close, the Aperture Effect will not result.

Figure 5:
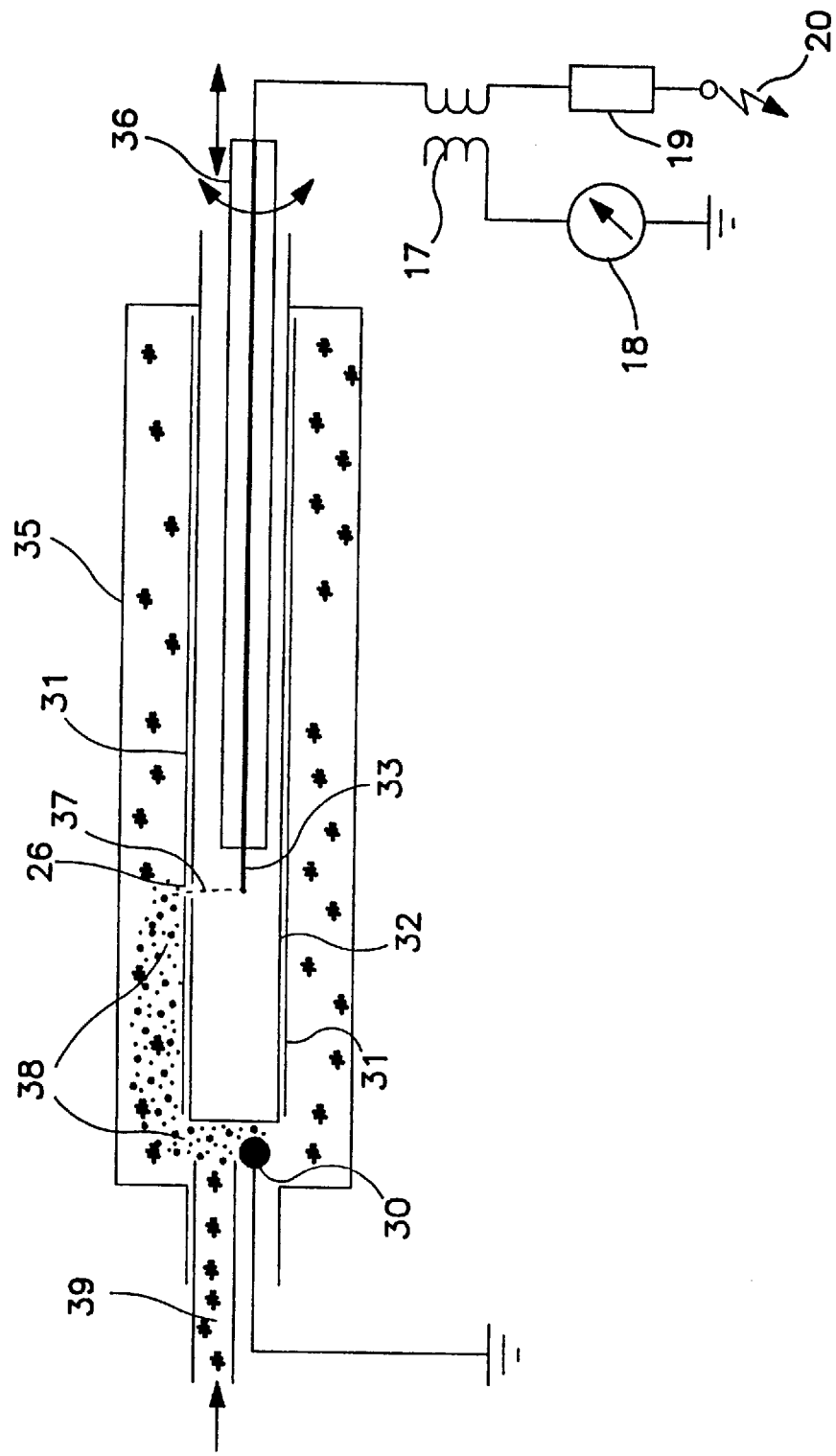
FIG. 5 is an exemplary circuit for determining the porosity of an encapsulated filter with a charged gaseous ground in accordance FIG. 1(a).
Figure 6:
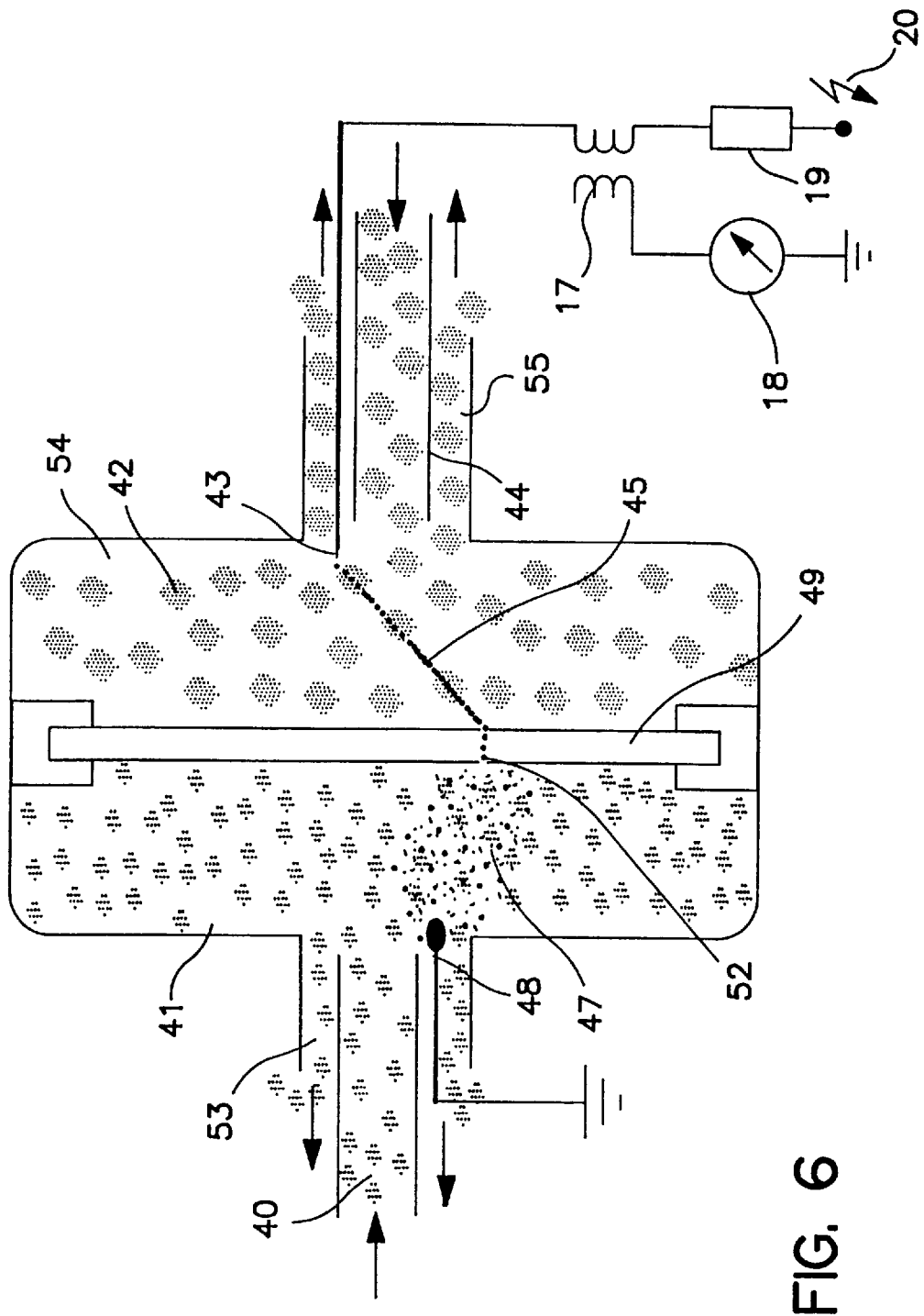
FIG. 6 is a further exemplary circuit for determining the porosity of an encapsulated filter with a charged gaseous ground in accordance FIG. 1(a).
Figure 7:
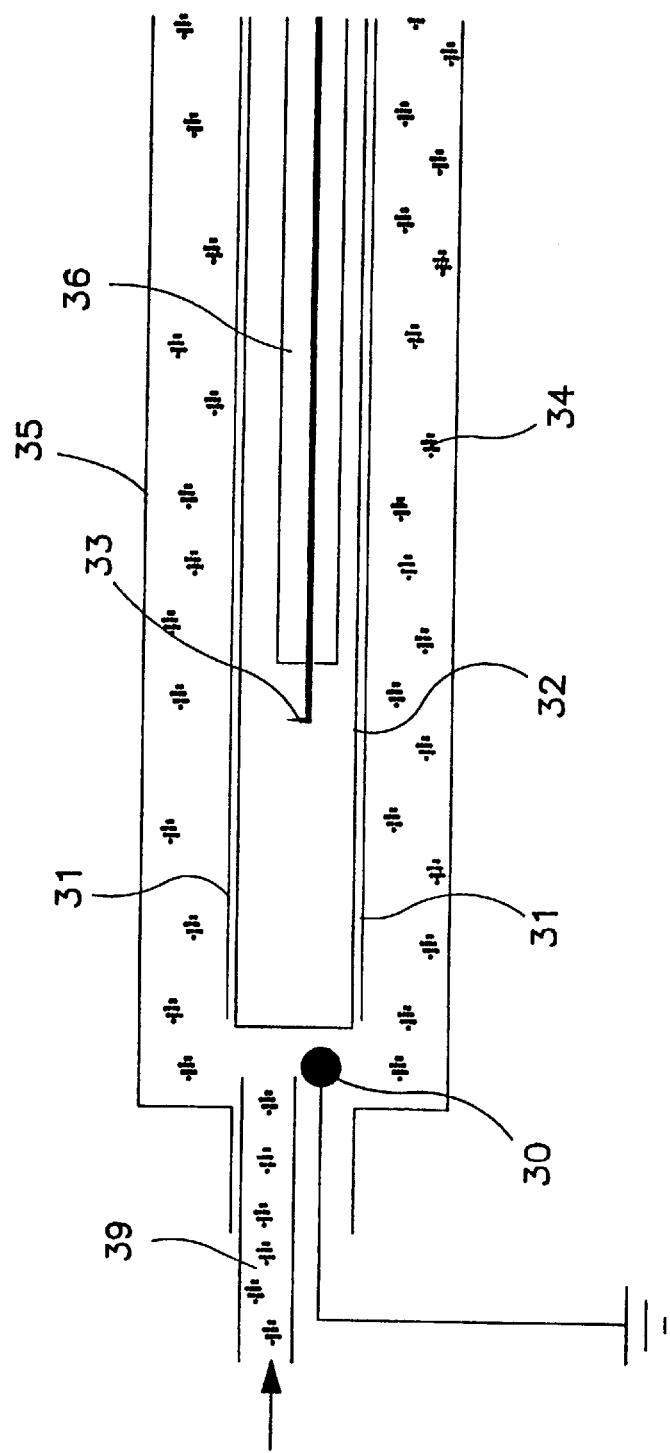
FIG. 7 is a schematic representation of an encapsulated filter that does not contain any holes or voids.

FIGS. 5–7 contain similar elements as have been described above with respect to FIG. 2. These elements are labeled identically and their description is omitted for brevity.

Referring to FIG. 5, there is shown a housing or a capsule 35 containing a filtration material 31. The filtration material 31 may be any type of an insulating (nonconductive) dielectric material used to filter out viral size particles. The filtration material 31 contacts the inner manifold 32 of the chamber. The capsule 35 is open on both ends. The filtration material is situated between the cathode 30, which is a flow of a noble gas that is being flushed into the capsule 35, and an anode 36. The anode 36 is slowly inserted into the inner section of the inner manifold 32 of the chamber, opposite to the cathode 30.

The product being tested in FIG. 5 is an encapsulated filter which may be used for filtering viruses out of the air for intravenous bags or for any other application where either the fluid or the air must be free of viral size particles. There is no metallic model or mandrel acting as a grounded cathode. Instead, an electrically charged conductive or neutral fluid acts as the grounded cathode 30 (a "gaseous ground") to create the flow of electrons to the anode 36, and to indicate the existence of a small hole 26 in the filtration material 31. Thus, this is similar to the effect described in FIG. 1(a). The electrically charged conductive or neutral fluid may be a noble gas, an alkaline gas, an acidic gas, a heated gas, or a conductive liquid. The electrically charged conductive or neutral fluid is flushed into the capsule 35 prior to flowing, or drawing, the electron beam, and may be flushed into the capsule 35 while the beam is being drawn.

In FIG. 5, electrons 38 are created by the cathode 30 charging the cover gas 39 which is being flushed into the capsule 35. Some of the electrons 38 flow through a small aperture or hole 26 in the filtration material 31 creating an electron flow 37. This electron flow 37 is attracted to the tip 33 of the anode 36 and gives rise to the Griebel-Gormley Aperture Effect. By measuring the electron flow 37, the size of the hole 26 may be determined.

It should be noted that the principle of the electrically charged conductive or neutral fluid ground which acts as a "gaseous ground" is based on Joseph Thomson's discovery of the conduction of electricity through gases, as described in a text by Thomson, "The Discharge of Electricity Through Gases" (Charles Scribner's Sons, 1898), which is incorporated herein by reference.

As the anode 36 is being inserted, it rotates and moves in and out. This motion is used, in conjunction with the directed flow of the cover gas 39, to detect a hole 26 in the filtration material 31. The detection of a hole 26 gives rise to the Aperture Effect.

It should be noted that the capsule as well as the sensor may be positioned using an automatic positioning device such as a servo motor, a stepper motor or a programmable positioning robot.

The construction of the anode 36 is as follows. The outside of the anode 36 consists of an insulating material such as nylon. The center of the anode 36 is a conductor which has the tip 33 angled to one side on it.

Referring to FIG. 6, there is shown a filtration material or membrane 49 in which each half of the chamber comprising the filtering product has a different modified atmosphere and may have different pressures. The membrane 49 is secured in the chamber or capsule such that the chamber is partitioned into two separate regions This differs from FIG. 5 in that FIG. 5 had one modified atmosphere (containing the cathode 30) and one open atmosphere (containing the anode 36).

In FIG. 6, cathode 48 is charging one modified atmosphere; i.e., charging one type of fluid as opposed to another fluid being on the opposite side of the filtration membrane 49. Because of an aperture or a hole 52 in the filtration membrane 49, the Griebel-Gormley Aperture Effect occurs from the charged fluid 47 to a fluidic medium 42 on the anode side. Anode 43 receives the electron flow 45 which is being monitored and measured.

On the cathode side of the filtration membrane 49, the fluid flows through the manifold 40 into the open chamber 41 and out of the outer housing 53. On the anode side of the filtration membrane 49, a different fluid 42 flows through the manifold 44 into the open chamber 54 and out of the outer housing 55.

Referring to FIG. 7, there is shown a capsule 35 containing a filtration material 31. This arrangement is similar to that shown in FIG. 5 and elements that have been described above with respect to FIG. 5 are labeled identically and their description is omitted. In FIG. 7, there is no abnormal hole in the filtration material 31. As a result, a baseline electron flow is generated by the cathode 30 and attracted to the tip 33 of the anode 36. Thus, no Aperture Effect is obtained, as described above with reference to FIG. 1(b). This filter would pass the porosity test because no hole or void is present beyond the prescribed baseline parameters.

The tip 33 of the anode 36 is pointed in a direction that is perpendicular to the surface of the inner manifold 32 of the chamber in order to create the point used to measure the flow of electrons if the Aperture Effect is present.

Figure 8:
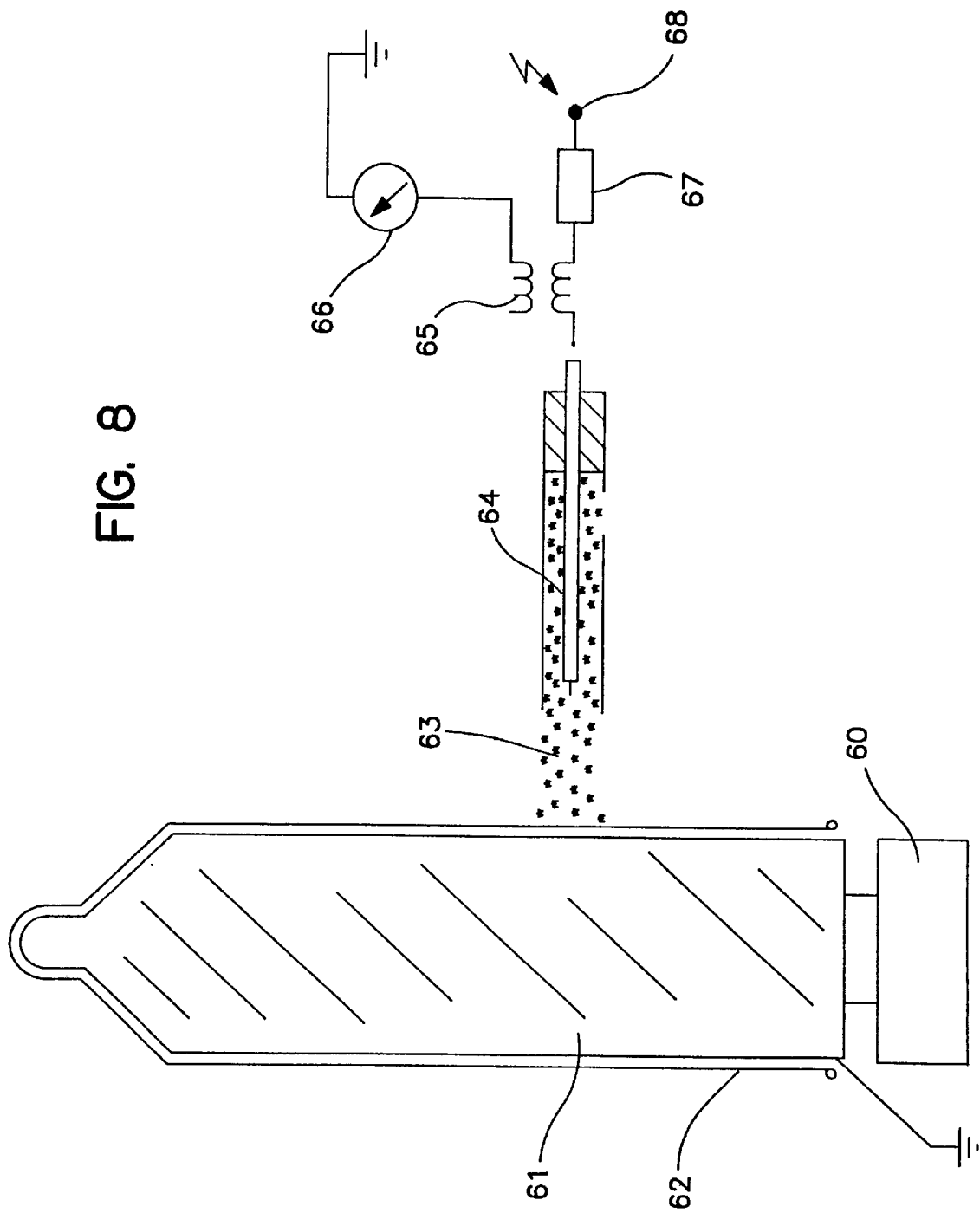
FIG. 8 is an exemplary circuit for an apparatus for determining the porosity of a condom in accordance with the present invention.

Referring to FIG. 8, there is shown an exemplary embodiment of an apparatus used to determine the porosity of a material by detection of the Griebel-Gormley Aperture Effect. We note that the present invention is performed in an open, non-chambered atmosphere. A nonconductive material, such as a latex condom 62, is placed on a model or mandrel 61 which is positioned by an automatic positioning device. Here, the mandrel 61 is rotated by a servo motor 60. In this embodiment, one sensor which is comprised of elements 64–68 is shown. A fluid cover gas 63 is also present.

The condom 62 rotates and the sensor elements 64 and 65 move up and down. In this manner, by the combined movements of the condom 62 and the sensor elements 64 and 65, a matrix is created and the entire surface area of the condom 62 has its porosity determined.

The operator may determine how quickly the mandrel 61 rotates and how quickly the sensor elements 64 and 65 move. As a result, the condom 62 may have its porosity determined as quickly or as slowly as the operator chooses. A typical porosity determination of an entire condom may be made in approximately one second or less.

The sensor elements 64 and 65 are an anode 64 and an antenna 65, respectively. The antenna 65 is a transformer with one open-ended side of the coil. The remaining sensor elements 66–68 are as follows: an ammeter 66, which in this embodiment would be a nanoammeter, a resistor 67 which is used to limit the current, and a high voltage connection 68.

The ammeter 66 shows proportionally the flow of current through the resistor 67 to the anode 64. The galvanic separation in the antenna 65 is where the current is detected. This current detection is done inductively as there is no actual connection between the two coils. It is very similar to a transformer but the detection coil is open to one side, which makes it an antenna very similar to those used in radio receivers. The ammeter 66 is grounded on one side in order to cause a current flow through the meter which will proportionately show the flow through the resistor 67 to the anode 64.

The above-described sensor at no time makes contact with the surface of the condom. It is a totally dry, non-destructive, non-interference method of testing the condom for holes, voids or anomalies. It is also a non-invasive method of testing. The speed of testing allows for several advantages over prior art. The condom can be tested in real-time, on-line without interfering with the manufacturing process, and the testing may be performed simultaneously with the manufacturing process. A much more thorough coverage of the surface area is obtained and each condom may be tested several times within a normal allotment of manufacturing line speed to a more precise degree of subviral porosity. The on-line, in real-time aspects of this testing method are critical because it is extremely cost effective and economical when the material that is being tested does not require rehandling. If there is a direct correlation between the sensing on-line after it is molded and a performance rate, then the quality of the end product would only have to be statistically sampled in order to prove efficacy for the market place.

Figure 9:
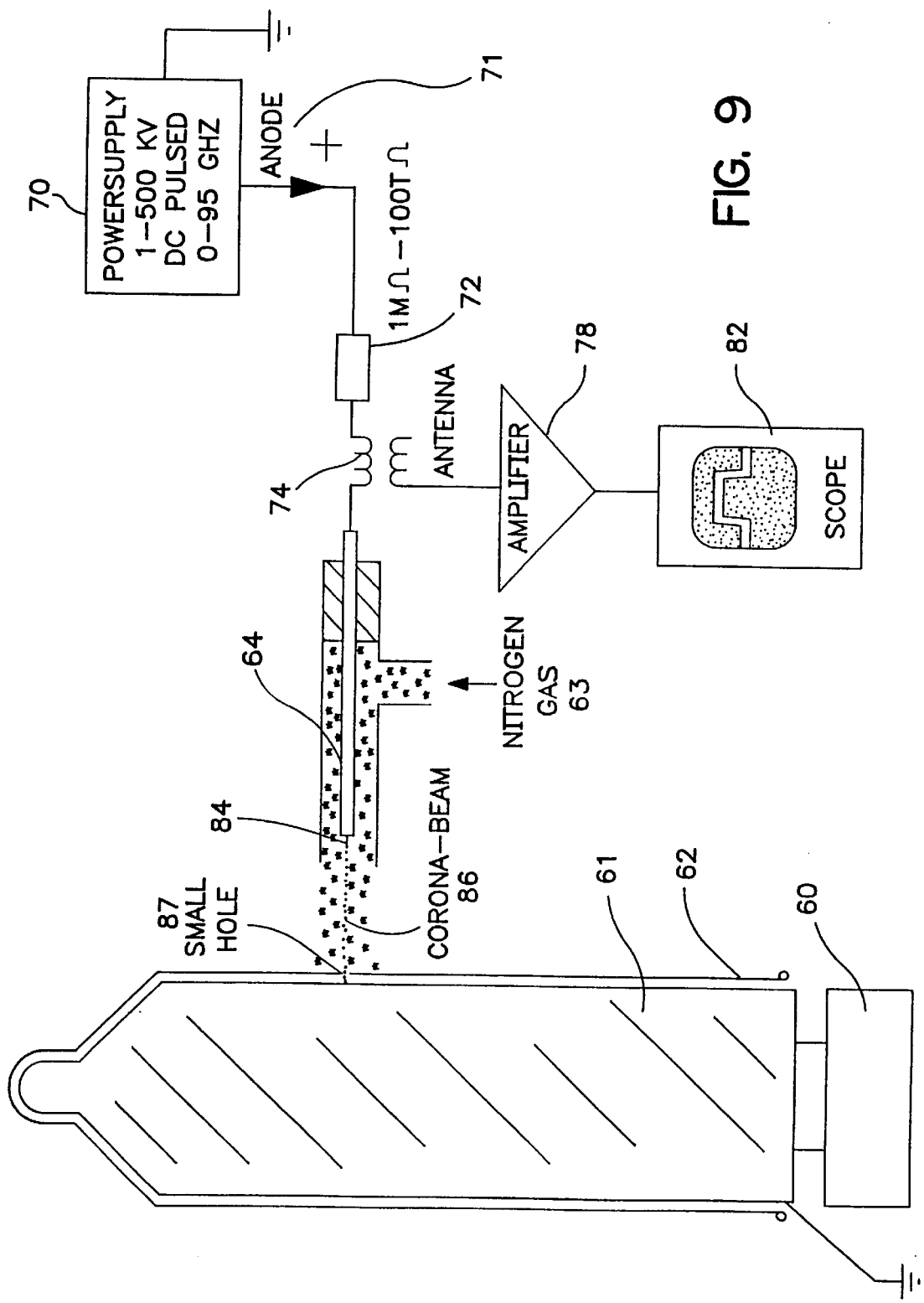
FIG. 9 is a further exemplary circuit for an apparatus for determining the porosity of a condom in accordance with the present invention.
Figure 10:
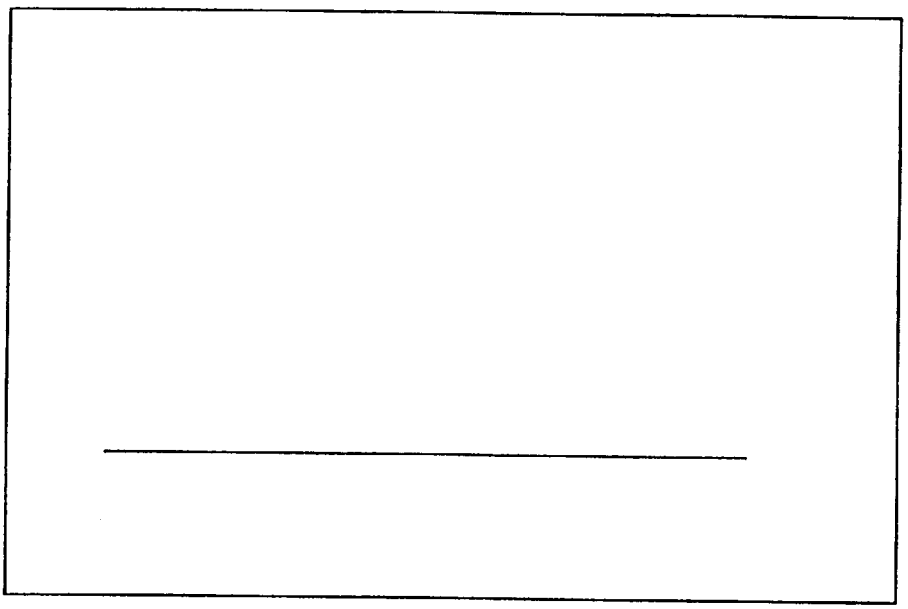
FIG. 10(a) is an exemplary wave form indicative of the presence of either no hole or a large hole in the material being tested.
FIG. 10(b) is an exemplary wave form indicative of the presence of a small hole in the material being tested.
Figure 10:
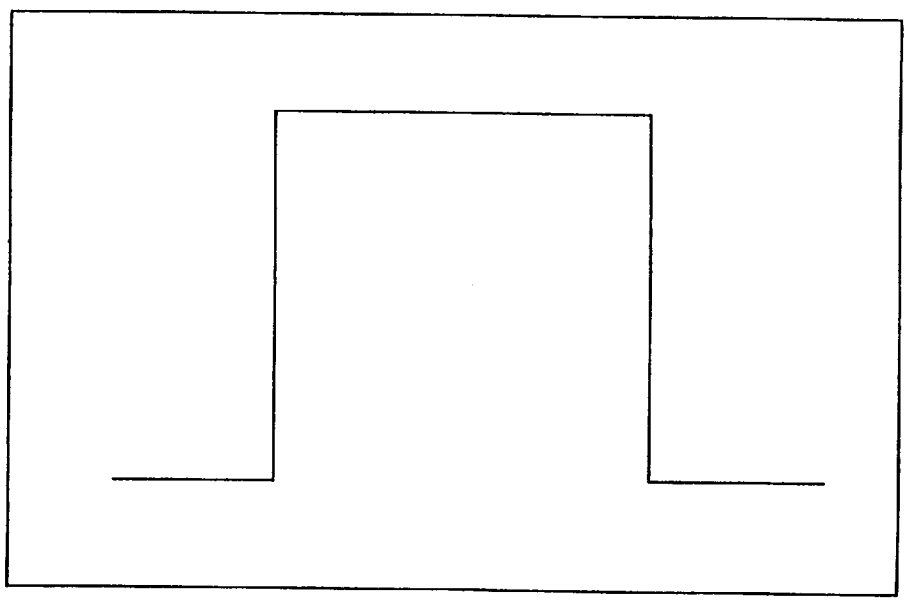
Figure 11:
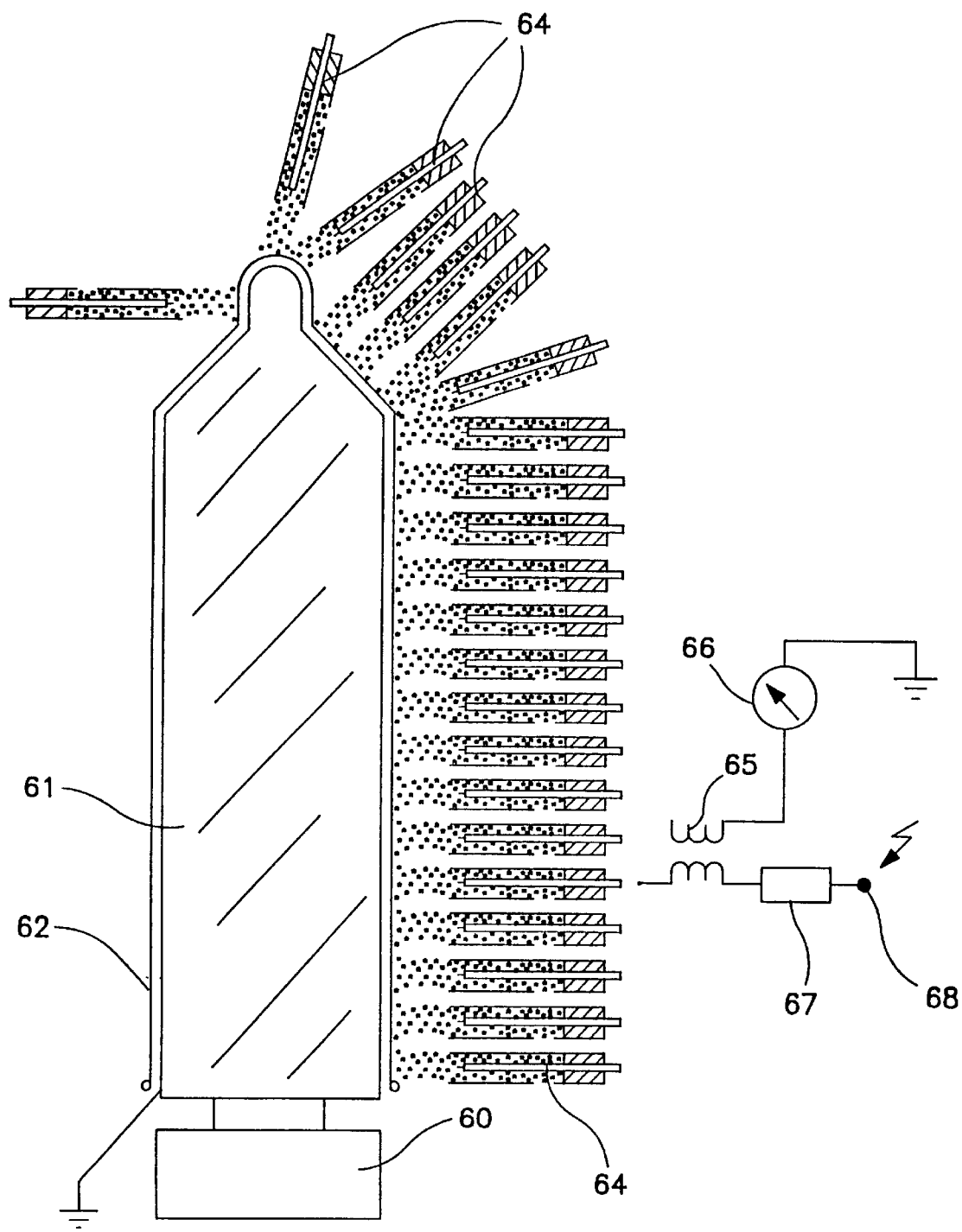
FIG. 11 is a further exemplary circuit using an array of sensors to determine the porosity of a condom in accordance with the present invention.

FIGS. 9, 11 and 13 contain similar elements as have been described above with respect to FIG. 8. These elements are labeled identically and their description is omitted for brevity.

Referring to FIG. 9, there is shown a further embodiment of the present invention with specific electronic measurement instrumentation. This embodiment is similar to the embodiment described above with reference to FIG. 8, however the measurement instrumentation differs.

A power supply 70 feeds current to a positive anode 71 which is connected to a high resistance resistor 72. The power supply 70 is a high voltage power supply which can range from 100 volts to 100 megavolts, with a preferred range of 1 to 500 kilovolts, pulsed D.C. at 0 to 95 GHz, or D.C. or A.C. The resistor 72 has a resistance from 1 kiloohm to 1000 teraohms. A preferred operating set of parameters is 32 kilovolts, 16 kHz D.C. pulsed, 30 gigaohms, and a nitrogen cover gas flow of 0.3 Lpm. The current flowing through the resistor 72 then flows through a galvanically separated coil or antenna 74. An amplifier 78 detects the current and is connected to an output oscilloscope 82. This integrated circuit is a millivolt amplifier that has a millivolt input and has a output of 0 to 3 volts D.C. The oscilloscope 82 shows the relative amount of electrons that are flowing from the positive anode 71 through the resistor 72 through the primary coil 74 to the tip 84 of the anode 64.

In this embodiment, a gaseous or vacuum predischarge distance could be used as the resistor 72. Such a resistor includes, for example, a cylinder filled with a gas or an evacuated cylinder.

In FIG. 9, a small hole 87 is present in the condom 62, and thus a corona beam 86 is generated.

The current as it leaves the power supply 70 is very strong and is dangerous. The resistor 72 reduces the current to the order of nanoamps. This reduction in current is necessary in order to detect a small change in current flow through the coil 74, which occurs during the presence of the Griebel-Gormley Aperture Effect. If resistor 72 were removed from the circuit, it would be difficult to detect a change in current flow through the coil 74 because a lot of stray electric fields would be generated by the strong field leaving the power supply 70 and destroy the material being tested. The material could be destroyed by an electrical avalanche that creates detrimental sparks.

Referring to FIG. 10(a), there is shown an exemplary waveform present on the oscilloscope 82 of FIG. 9 when either no hole or a large hole in the material is detected by the sensor of FIG. 9.

Referring to FIG. 10(b), there is shown an exemplary waveform present on the oscilloscope 82 of FIG. 9 when a small hole is detected in the material by the sensor of FIG. 9.

Referring to FIG. 11, there is shown a further exemplary embodiment of the present invention. This embodiment comprises an array of multiple sensors; here, 22 sensors are represented. Each of the anodes 64 is connected to the sensor circuitry, elements 65–68. The servo motor 60 turns the mandrel 61 on which the condom 62 is placed. However, there is no vertical motion of the anodes 64 and antennae 65 over the condom.

The operator of this embodiment can be notified of the detection of a hole in several different ways. One way is to attach an oscilloscope to each particular sensor circuitry, as is described above with reference to FIG. 9. However, this method would be cumbersome as it would require many oscilloscopes. A preferred method of notifying the operator of the detection of a hole in the condom is attaching detection amplifiers to a high speed latch circuit. Whenever there is increased flow of electrons in the sensing device, the latch latches under this very quickly, on the order of less than 10 nanoseconds, and remains latched. The machine operator knows which sensing device was triggered and therefore has found a defect in that sensing area. The machine operator then stops the machine and removes the defective condom, and resets the sensors so that all the latches are open again and the next condom may be tested. This is an inexpensive method of testing a material such as a condom for a hole or void, but it has the disadvantage of not being able to detect blisters or is bubbles in the material.

Figure 12B:
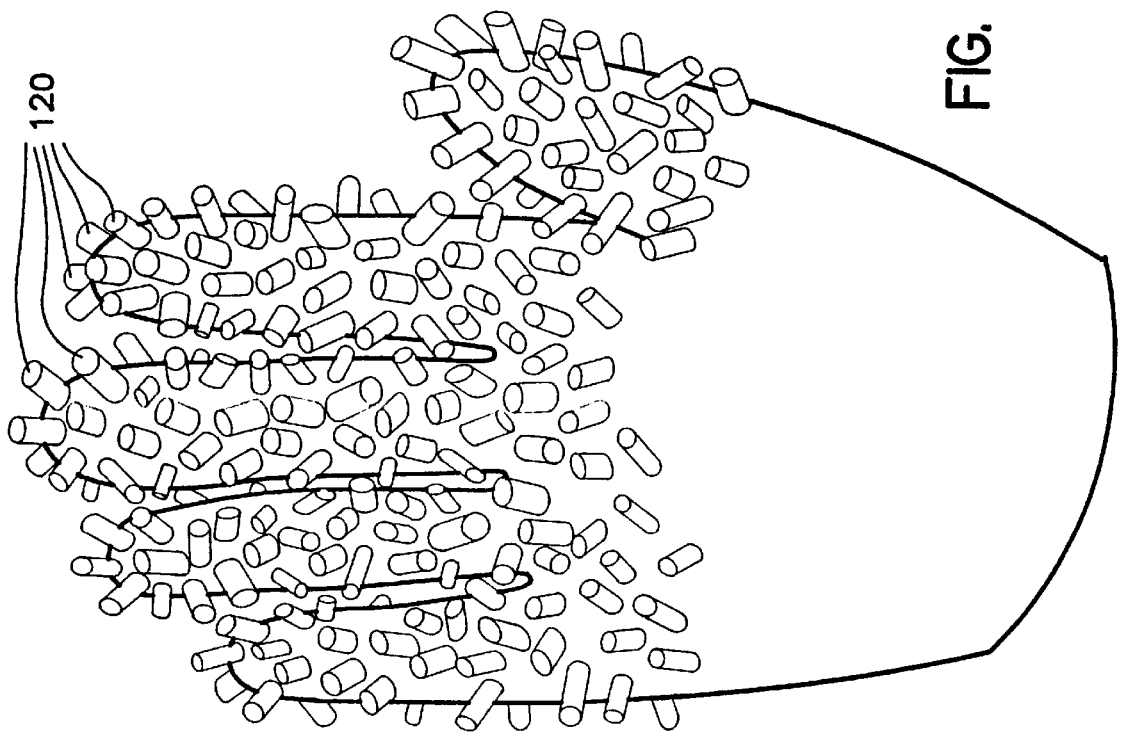
FIG. 12(b) shows an outside female glove mold to determine the porosity of a nonconductive barrier glove in accordance with the present invention.
Figure 12A:
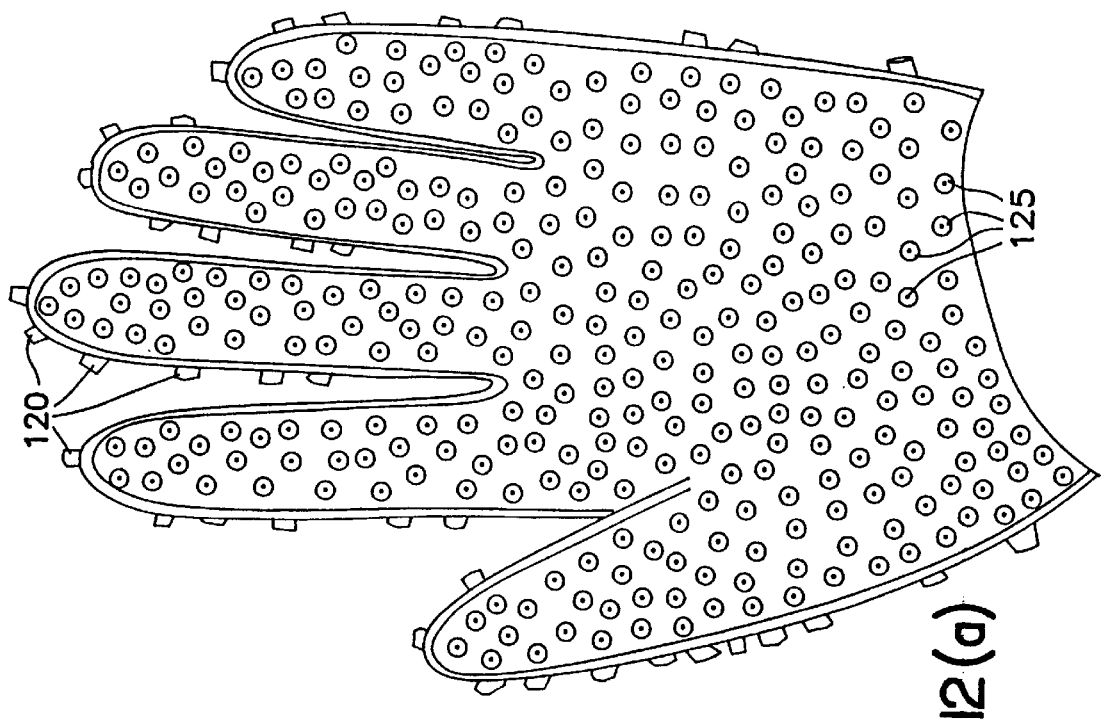
FIG. 12(a) is an exemplary embodiment, showing an inside female glove mold, to determine the porosity of a nonconductive barrier glove in accordance with the present invention.
Figure 13:
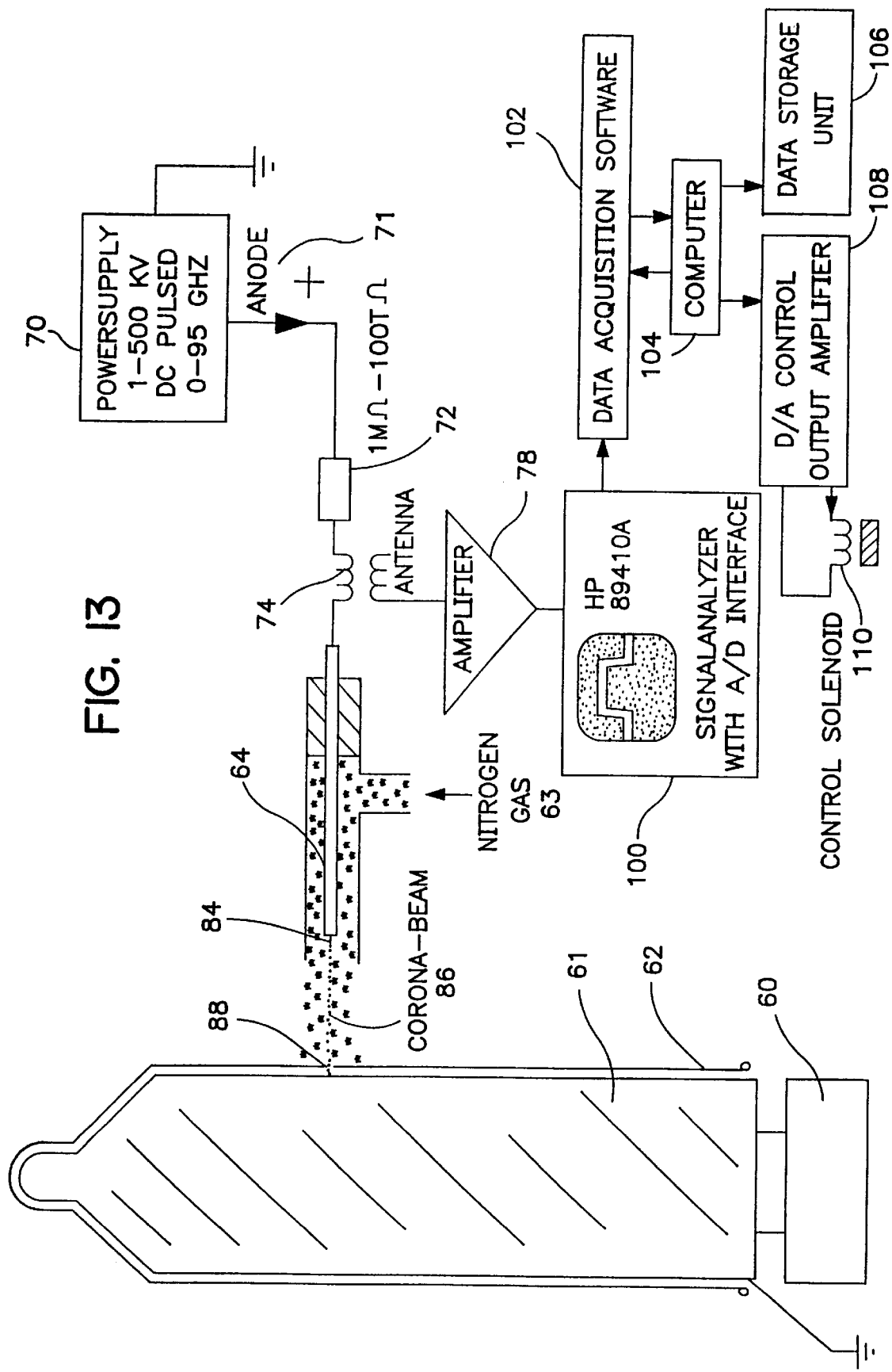
FIG. 13 is a further exemplary circuit using a Signal Analyzer to determine the porosity and to detect non-void material anomalies of a condom in accordance with the present invention.

Referring to FIGS. 12(a) and 12(b), there is shown a further exemplary embodiment of the present invention. This embodiment may be used to detect the presence of holes or voids in a nonconductive barrier glove, such as a latex or rubber glove of the type used in the medical field. The glove to be tested is placed on a male mandrel (not shown). The male mandrel closely matches the dimensions of the glove to be tested. The remainder of the testing station includes a female mold of the glove that contains the individual sensors and circuitry for detecting any holes or voids in the material being tested.

FIG. 12(a) shows an inside view of the female glove mold. FIG. 12(b) shows an outside view of the female glove mold. In this application, there is a large number of sensors 120, on the order of up to 300 or possibly more. These sensors 120 penetrate the female mold as shown in FIG. 12(a), terminating with anode points 125 in the interior of the female mold. These anode points 125 permit the electron beam to interact with the glove being tested.

The sensors 120 move over the male mandrel containing the glove and encapsulate it for a short period of time. During this encapsulation, a static measurement occurs (i.e., no movement or rotation of the male mandrel and glove). Each one of the sensors 120 in the female mold takes a reading and determines whether the glove is acceptable or not acceptable. If the glove passes inspection, it is sent to a packaging station.

Referring to FIG. 12(c), there is shown a further exemplary embodiment of the present invention. This embodiment, like that shown in FIGS. 12(a) and 12(b), is also used to detect the presence of holes or voids in a latex or rubber glove of the type used in the medical field. The glove to be tested is placed on a male mandrel 130 and positioned using an automatic positioning device such as a stepper motor, a servo motor or a programmable robot. Here, the mandrel 130 is rotated by a servo motor 135. The male mandrel 130 closely matches the dimensions of the glove to be tested. The remainder of the testing station includes an articulating robotic arm 140 that positions itself around the male mandrel 130. The robotic arm 140 contains a sensor 145 and circuitry for detecting any holes or voids in the material being tested.

The robotic arm 140 moves the sensor 145 up and down, and left and right over the glove being tested, as the glove is rotated by the servo motor 135. The sensor 145 takes a reading at each point of the glove being tested and determines whether the glove is acceptable or not acceptable. If the glove passes inspection, it is sent to a packaging station.

It should be noted that the embodiment disclosed in FIGS. 12(a) and 12(b) is more expensive than the embodiment disclosed in FIG. 12(c). However, the embodiment in FIGS. 12(a) and 12(b) is able to test a glove in a few seconds, whereas the embodiment in FIG. 12(c) takes about 1 minute to test a glove. It is desirable to use the quicker embodiment in a production process.

FIG. 13 contains similar elements as have been described above with respect to FIG. 9. These elements are labeled identically and their description is omitted for brevity.

Referring to FIG. 13, there is shown a further exemplary embodiment of the present invention which contains the measurement instrumentation desirable to detect an anomaly 88 existing in a nonconductive material. An anomaly includes blisters, bubbles, uncured areas, material differentiations including the presence of foreign materials, inconsistency in production process and anything that is not calibrated to a standard. An anomaly may lead to failure of the material during use.

It should be noted that the below described detection circuitry can be adapted for use with the monitoring embodiments in FIGS. 2–12(c). Accordingly, the embodiments in FIGS. 2–12(c) can be used to detect the presence of anomalies, as well as holes, in a material.

In this embodiment, a signal analyzer 100 (a Hewlett Packard Signal Analyzer Model 89410A is shown) analyzes the changes in frequencies and harmonics. The pulsed power supply 70 provides a working frequency on the order of 0 to 95 GHz or D.C. or A.C. However, as soon as a corona beam 86 starts to flow, indicating the presence of a material anomaly, there is a disturbance in the field. This disturbance ranges up to the gigahertz frequency level. Many harmonics and overtones are formed, as well as many constructive and destructive interference between the frequencies. These frequencies, harmonics and overtones are analyzed with the signal analyzer 100.

The output of the signal analyzer 100 is sent into a fast analog/digital interface (not shown) that is connected to a computer 104 containing data acquisition software 102. The computer 104 stores the data in a data storage unit 106.

The software 102 analyzes the signal and compares it to various predetermined parameters. After this comparison is made, the software 102 either accepts the material as containing no harmful anomalies or rejects the material as containing at least one of the above-listed material anomalies.

The software 102 sends the "accept" or "reject" decision through the computer 104 to a digital/analog converter and amplifier 108 where the analog signal is amplified to a level that drives a control solenoid 110 which sends the material on for either packaging or disposal.

It is preferable to perform multiple readings, each reading at a different power supply frequency, and, using the data acquisition software 102, compare the results of the readings. Comparison of readings performed at different frequencies decreases resonance and feedback problems inherent in one individual reading.

The actual power or energy that is used to test the material in the present invention is much smaller (about 3000–4000 times smaller) than what is necessary to damage the material being tested (e.g., latex, urethane, etc.). For example, a latex condom or glove is exposed to about 5 nanowatt-hours of energy. It would take several thousand times this quantity of watt-hours to damage or burn the material, thus rendering the material defective.

It should be noted that the anode and cathode can be reversed in the aforementioned exemplary embodiments without any deterioration in the quality of the testing and measuring of the nonconductive material. Thus, for example, the mandrel (which was described in the above embodiments as a cathode) may be used as the anode while the tip that was used as to attract electrons may be used as the cathode to expel electrons. However, a cathodic corona is more destructive than an anodic corona.

Figure 14:
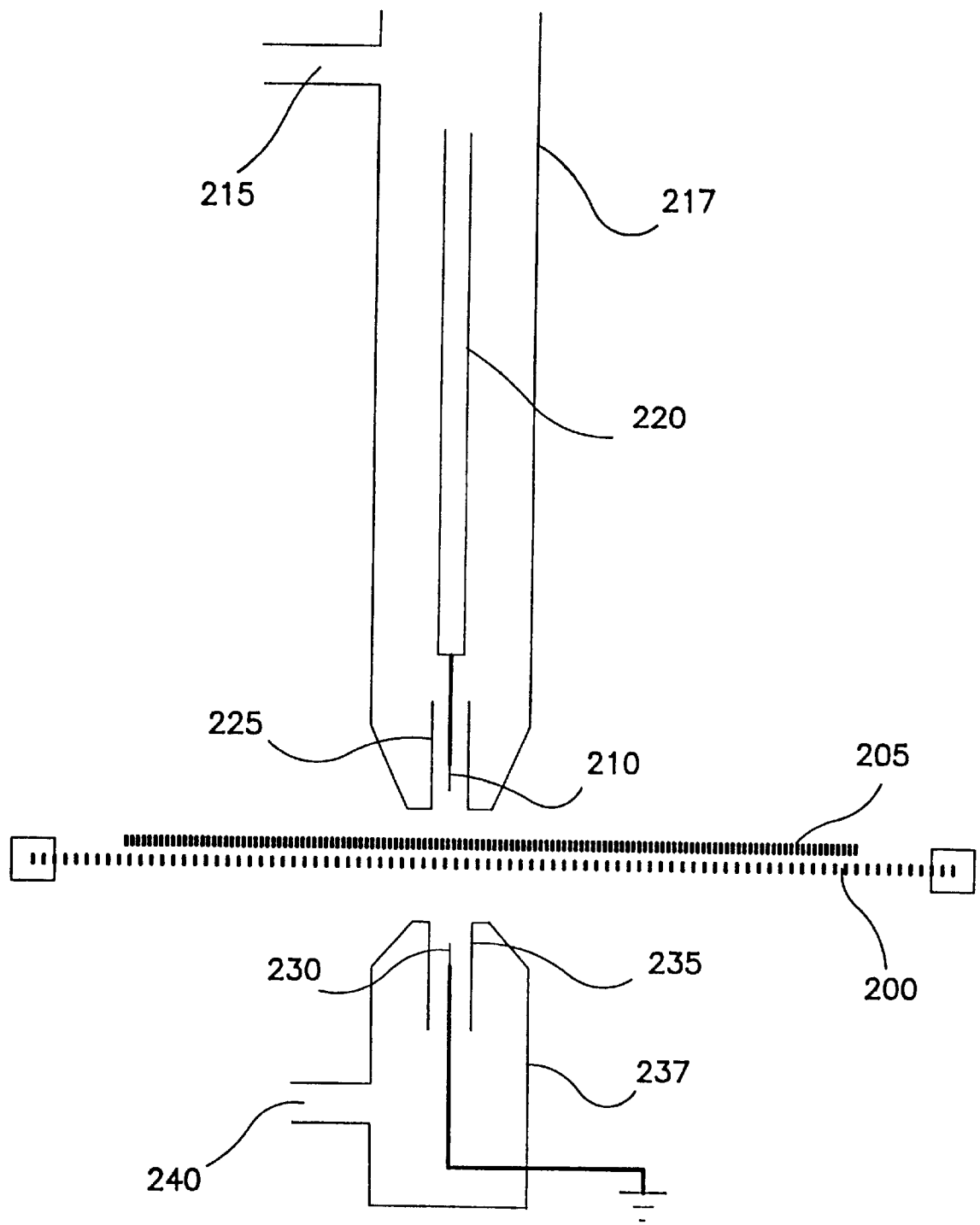
FIG. 14 is a schematic representation of an exemplary embodiment using a coarse dielectric screen.

Another embodiment according to the present invention is shown in FIG. 14. The anode side of this embodiment is similar to that shown in FIG. 1(a) in that it has a gas 215 introduced into a housing 217 enclosing an anode 220. The anode 220 ends in a point 210 at a jet 225 at an end of the housing 217. In this embodiment, a coarse dielectric screen 200, such as nylon, replaces the smooth, rounded conductive model, such as the metal mandrel, used in the previously described embodiments. A barrier material 205 to be tested is placed on top of the nylon screen 200. On the cathode side, instead of having a flat ground underneath it, a grounded point 230 is placed underneath the screen 200. The point 230 extends between a jet 235 out of the cathode housing 237. The point 230 does not contact the screen 200. The screen 200 is approximately in the center of the two points 210 and 230. However, the screen 200 can be placed against the cathode. The points 210 and 230 are preferably about onehalf inch apart, but this distance can vary. A gas 240 is introduced in the housing 237 on the cathode side. Thus, gas, preferably nitrogen or a noble gas, flows from both the anode side as well as the cathode side. An improved effect is obtained when noble gases instead of nitrogen are used. This embodiment permits the detection of holes below 2 nm, on the order of about 5 angstroms. This is considered molecular diffusion.

Molecular diffusion is the transfer of mass between adjacent layers of fluid in laminar flow. With respect to the present invention, the corona beam flows electrons through a solid material that is being tested. At areas in the solid material where the molecular cross-linking is weaker than other areas, the electrons will pass through more easily. The portion of the material where the electrons pass through more easily reveals the portion of the material that is more permeable to molecules, i.e., that are more susceptible to molecular diffusion. This is considered to be another type of anomaly.

It should be noted that a vacuum, rather than a gas flow, can be used on the cathode side. The vacuum allows the electrons to flow with greater ease and assists the barrier material 205 in remaining fixed on the nylon screen 200.

The cathode can be heated. This facilitates the movement of electrons with greater ease through the anomalies of the material that is being tested. Also, an improvement in signal to noise ratio is created.

FIGS. 15(a), 15(b), 16, and 17 contain similar elements as have been described above with respect to FIG. 14. These elements are labeled identically and their description is omitted for brevity.

Figure 15:
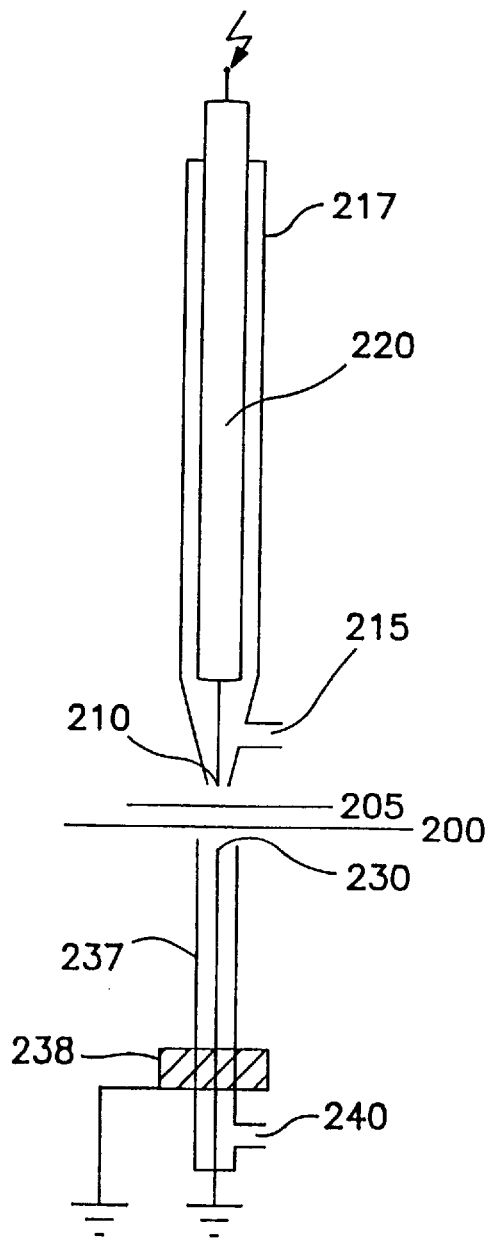
FIGS. 15(a) and 15(b) are schematic representations of an exemplary embodiment using a field strength and angle attenuator ring.
Figure 15:
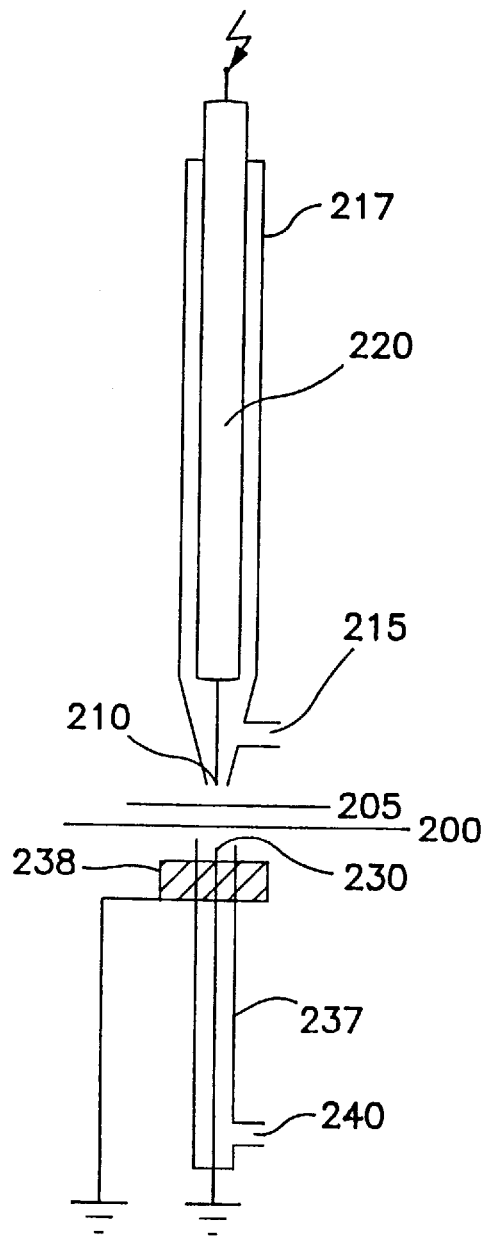

A field strength and angle attenuator ring can be implemented underneath the nylon screen in the embodiment shown in FIG. 14. An exemplary embodiment of the present invention which includes a field strength and angle attenuator ring 238 is shown in FIGS. 15(a) and 15(b). The ring 238 surrounds the jet 235 and is conductive and grounded. The ring 238 can be placed anywhere on the cathode, either near the tip, as shown in FIG. 15(b), or far down the cathode shaft, as shown in FIG. 15(a).

The field strength and angle attenuator ring 238 spreads the field intensity around the point 230 on the cathode. In other words, the ring 238 lowers the field intensity and the intensity of the discharge. This is important when using a very thin, easily destructible material such as the nylon screen 200 and the test material. The lowered field intensity also results in a more restricted area in which an anomaly can be detected. Thus, the ring 238 causes the electrons to focus into a tighter area. This facilitates the detection of nanometer-and sub-nanometer-anomalies. The ring 238 results in a greater focus of electrons and more of a focal point as the ring 238 gets closer to the end of the cathode tip.

Figure 16:
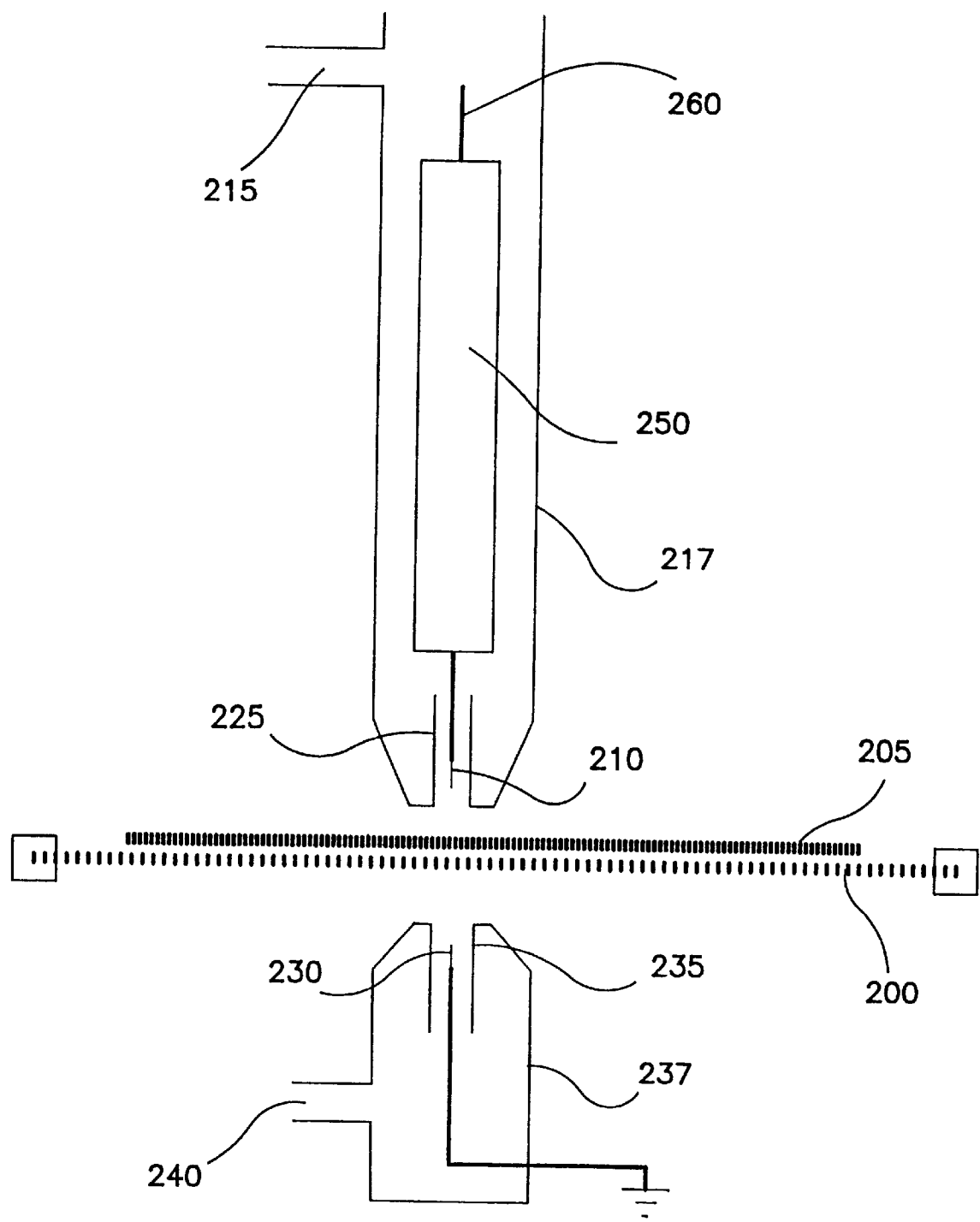
FIG. 16 is a schematic representation of an exemplary embodiment using a large focusing resistor.

Another embodiment according to the present invention is shown in FIG. 16. In this embodiment, a very large resistor 250 is used as a focusing resistor between the power supply 260 and the sensor point 210. A resistor in the range of 1 kiloohm to 1000 teraohms is used. A preferred resistance range is 30 to 90 gigaohms. The focusing resistor adjusts the tightness, or width, of the electron beam. Moreover, 32 kV of filtered D.C., no frequency, is used as the power supply 260. A preferred operating set of parameters is 32 kilovolts, D.C., 90 gigaohms, and a nitrogen cover gas flow of 1.0 Lpm. As the voltage is increased, smaller material anomalies can be detected because with an increased voltage, the focusing resistor 250 can be increased. This enables the discharge to be a very narrow beam of electrons. This technique may be used with a grounded metal plate as well as the nylon screen 200 shown.

When an anomaly is detected, the voltage resonates at a frequency, waveshape and amplitude that is determinative of the size and kind of anomaly. The higher the voltage that is used, the smaller the hole that can be detected. However, this increased voltage becomes more destructive. The large resistor 250 restricts the flow of electrons but does not reduce the voltage. The voltage on the tip 210 of the sensor remains the same. Thus, the energy is kept very low, thereby reducing the destructiveness of the beam. A power supply of 300 kV can be used with a focusing resistor in the high gigaohms range to detect even smaller anomalies.

Due to the high voltages, the beam length increases to the order of about six inches. This is important in a filter housing in which a long flexible length is desired to test every crevice, for example, in a fan-folded material. It is also useful for measuring gloves and other structures with complex geometries. With a 500 kV power supply, a noble gas, and a 2 teraohm focusing resistor, the beam length can be increased up to 10 inches. These high voltages are desirably insulated from each other.

Figure 17:
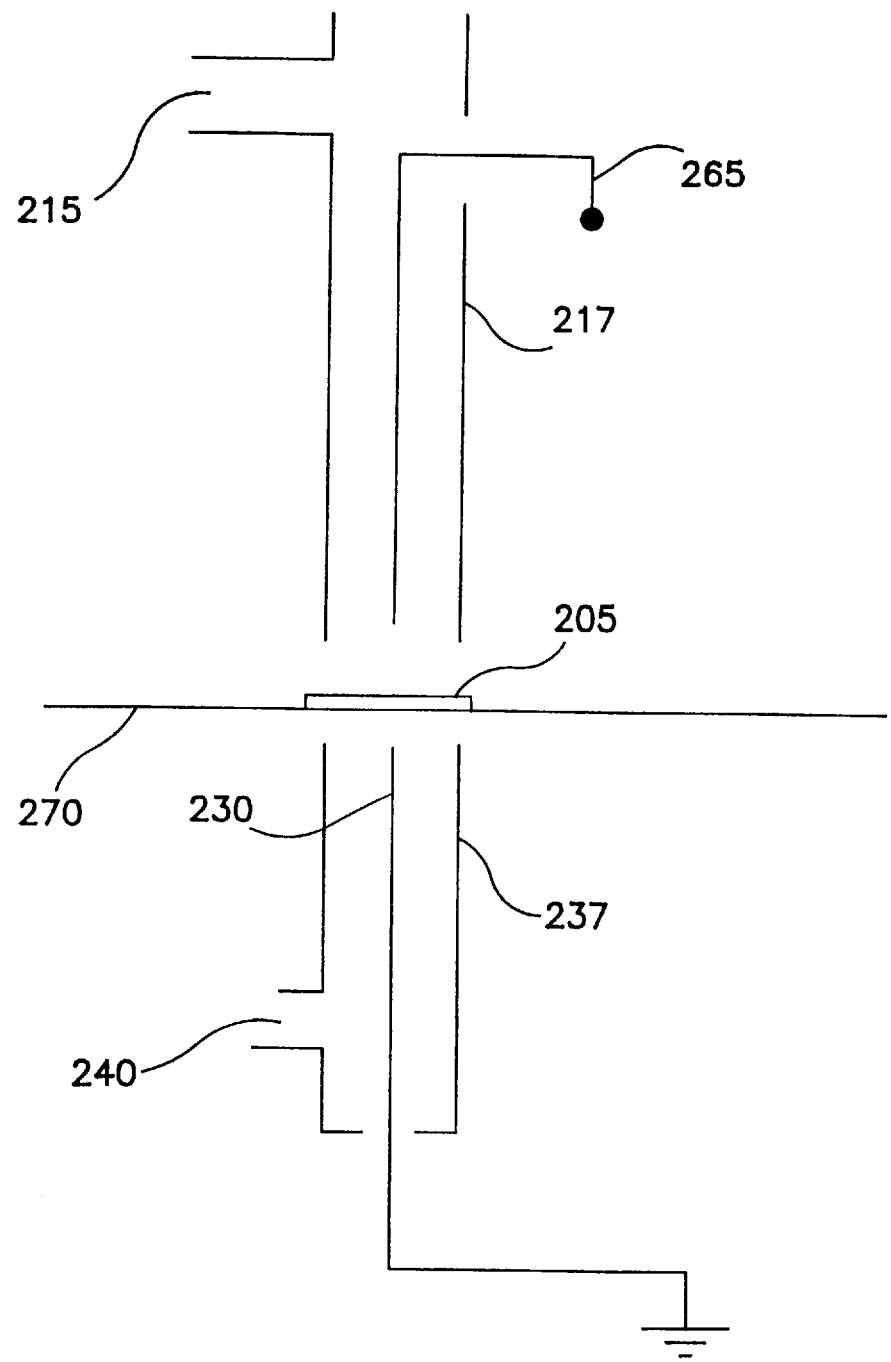
FIG. 17 is a schematic representation of an exemplary embodiment using an anomaly-free dielectric film.

Another embodiment according to the present invention is shown in FIG. 17. A high voltage anode 265 is used as the power supply. A material 205 which is being tested for the presence of anomalies is placed on an anomaly-free dielectric film 270. As the material 205 is being tested, a capacitance builds up and the electrons in the anomalies of the material 205 begin to resonate. The capacitance discharges through the dielectric film 270. No anomalies are created in the dielectric film 270, but the Aperture Effect is still present and detectable. This embodiment is desirable because the fabrication of some barrier materials, such as rubber gloves or condoms, employs two dipping applications. If the first application produces an anomaly-free material, the second application of the material can still be tested using this exemplary embodiment. Thus, both dipping applications can be tested to detect the presence of an anomaly, such as a hole, blister, or spongy area.

Depending on the frequency, amplitude and waveshape of the signal, it can be determined whether the anomaly is a hole or another type of structural anomaly such as a blister.

Figure 18:
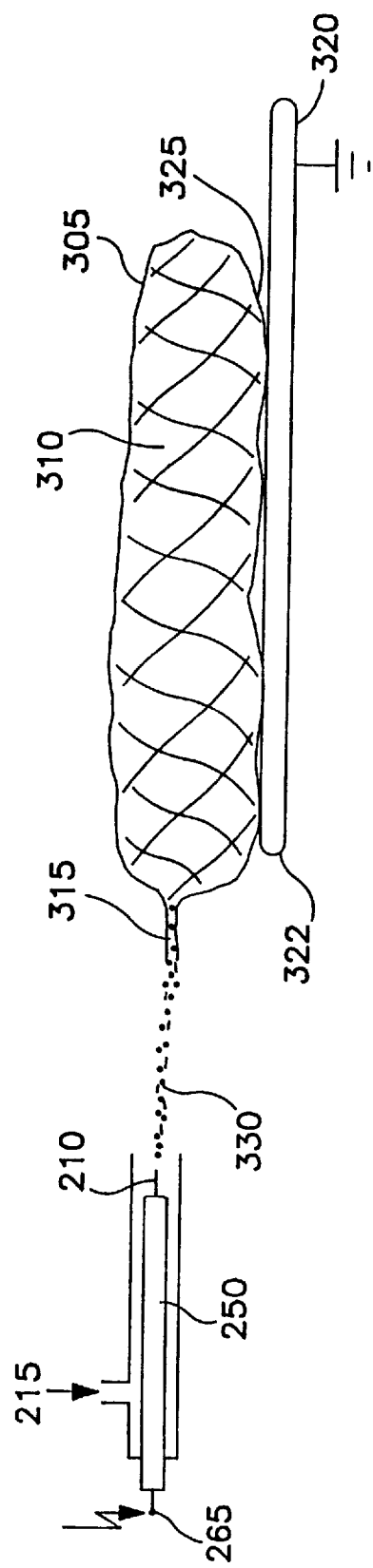
FIG. 18 is a schematic representation of an exemplary embodiment using a dielectric bag.

FIG. 18 contains similar elements as have been described above with respect to FIGS. 16 and 17. These elements are labeled identically and their description is omitted for brevity.

Another embodiment according to the present invention is shown in FIG. 18. A dielectric bag 305 is being tested for the presence of an aperture 315. The dielectric bag 305 contains a conductive content 310. The dielectric bag is placed on a grounded conductive plate 320 having a rounded edge 322 to form a capacitive connection 325 between ground and the conductive content 310. Electrons 330 are drawn from the conductive content 310 of the dielectric bag 305 through an aperture 315 in the dielectric bag 305. These electrons are sensed at the sensor point 210 of the anode. Thus, an aperture in a dielectric bag is detected.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A method for the non-destructive testing and detecting of at least one of a porosity and an anomaly in a material, comprising the steps of:
   (a) disposing the material on a conductive model;
   (b) generating a point-to-point effect by:
      (i) flowing an electron beam in an open atmosphere through a fluid cover gas between a first conductor point and a second conductor point through the porosity or the anomaly in the material, the second conductor point being formed on the conductive model at the porosity or the anomaly, and
      (i) resisting the flow of electrons to control the size of the electron beam sufficiently to prevent avalanche discharge; and
   (c) measuring at least one of an electric discharge and a change in an electric field with a sensor, thereby to detect the porosity or anomaly.

2. The method of claim 1 wherein the conductive model is one of a mandrel, a plate, a roller, and a point.

3. The method of claim 1 wherein the fluid cover gas is one of nitrogen, a noncombustible gas, a noble gas, and dehydrated air.

4. The method of claim 2 further comprising the step of: positioning one of the conductive model and the sensor using an automatic positioning device while flowing the electron beam.

5. The method of claim 4 wherein the automatic positioning device is one of a servo motor, a stepper motor, and a programmable positioning robot.

6. A method for the non-destructive testing and measuring of at least one of a porosity and an anomaly in a material, comprising the steps of:
   disposing the material on a conductive model;
   generating a point-to-point effect by flowing an electron beam between a first conductor point and a second conductor point through the porosity or the anomaly in the material, the second conductor point being formed on the conductive model at the porosity or the anomaly; and
   measuring at least one of an electric discharge and a change in an electric field with a sensor,
   further comprising the steps of:
      securing the material as a partition in a capsule;
      flushing a first side of the partition with an electrically charged conductive or neutral fluid;
      introducing a fluid cover gas from a second side of the partition; and
      the step of flowing the electron beam includes flowing the electron beam through the fluid cover gas between a source of the beam and the porosity or the anomaly in the material.

7. The method of claim 6 wherein the electrically charged conductive or neutral fluid is one of a noble gas, an alkaline gas, an acidic gas, a heated gas, and a conductive liquid.

8. The method of claim 6 wherein the fluid cover gas is one of nitrogen, a noncombustible gas, a noble gas, and dehydrated air.

9. The method of claim 6 further comprising the step of: positioning one of the capsule and the sensor using an automatic positioning device while flowing the electron beam.

10. The method of claim 9 wherein the automatic positioning device is one of a servo motor, a stepper motor, and a programmable positioning robot.

11. The method of claim 1 wherein the anomaly is one of a contaminant, a blister, a bubble, an uncatalyzed resin, an unblended resin, a low density material, a material having a weak molecular crosslinking strength, a high density material, an overlapping material, a formation defect and a stress fracture.

12. The method of claim 1 wherein the step of resisting the flow of electrons to control the size of the electron beam uses a focusing resistance means having a resistance value between 1 kiloohm and 1000 teraohms.

13. The method of claim 12 wherein the resistance value has a preferred range of 30 gigaohms to 90 gigaohms.

14. The method of claim 1 wherein the step of flowing the electron beam includes:
   flowing the electron beam between a dielectric material, disposed above the first conductor point, and the second conductor point through the porosity or the anomaly in the material.

15. The method of claim 14 wherein a field strength and angle attenuator ring is disposed around the second conductor point.

16. The method of claim 14 further comprising the step of:
   disposing the dielectric material between the material and the conductive model; and
   the step of flowing the electron beam includes flowing the electron beam through a first fluid cover gas between a source of the electron beam and the porosity or the anomaly in the material.

17. The method of claim 16 wherein the step of flowing the electron beam includes flowing the electron beam through a vacuum between the second conductor point and the dielectric material.

18. A method for the non-destructive testing and measuring of at least one of a porosity and an anomaly in a material, comprising the steps of:
   disposing the material on a conductive model;
   disposing a dielectric material between the material and the conductive model, the dielectric material being disposed above a first conductor point; and
   generating a point-to-point effect by flowing an electron beam between the first conductor point and a second conductor point through the porosity or the anomaly in the material, the second conductor point being formed on the conductive model at the porosity or the anomaly, wherein the step of flowing the electron beam includes:
      flowing the electron beam between the dielectric material and the second conductor point through theporosity or the anomaly in the material,
      flowing the electron beam through a first fluid cover gas between a source of the electron beam and the porosity or the anomaly in the material, and
      flowing the electron beam through a second fluid cover gas between the second conductor point and the dielectric material; and
   measuring at least one of an electric discharge and a change in an electric field with a sensor.

19. The method of claim 18 wherein each one of the first fluid cover gas and the second fluid cover gas is one of nitrogen, a noncombustible gas, a noble gas, and dehydrated air.

20. A method for the non-destructive testing and measuring of at least one of a porosity and an anomaly in a material, comprising the steps of:

disposing the material on a conductive model;

disposing a dielectric material between the material and the conductive model, the dielectric material being disposed above a first conductor point; and generating a point-to-point effect by flowing an electron beam between the first conductor point and a second conductor point through the porosity or the anomaly in the material, the second conductor point being formed on the conductive model at the porosity or the anomaly, wherein the step of flowing the electron beam includes:

flowing the electron beam between the dielectric material and the second conductor point through theporosity or the anomaly in the material, flowing the electron beam through a first fluid cover gas between a source of the electron beam and the porosity or the anomaly in the material, and wherein the dielectric material is positioned between the first conductor point and the second conductor point; and measuring at least one of an electric discharge and a change in an electric field with a sensor.

21. A method for the non-destructive testing and measuring of at least one of a porosity and an anomaly in a material, comprising the steps of:

disposing the material on a conductive model;

disposing a dielectric material between the material and the conductive model, the dielectric material being disposed above a first conductor point; and generating a point-to-point effect by flowing an electron beam between the first conductor point and a second conductor point through the porosity or the anomaly in the material, the second conductor point being formed on the conductive model at the porosity or the anomaly, wherein the step of flowing the electron beam includes:

flowing the electron beam between the dielectric material and the second conductor point through theporosity or the anomaly in the material, flowing the electron beam through a first fluid cover gas between a source of the electron beam and the porosity or the anomaly in the material, and wherein the dielectric material is one of a nylon screen and an anomaly-free dielectric film; and measuring at least one of an electric discharge and a change in an electric field with a sensor.

22. A method for the non-destructive testing and measuring of at least one of a porosity and an anomaly in a material, comprising the steps of:

disposing the material on a conductive model;

generating a point-to-point effect by: flowing an electron beam between a first conductor point and a second conductor point through the porosity or the anomaly in the material, the second conductor point being formed on the conductive model at the porosity or the anomaly, wherein the step of flowing the electron beam includes flowing the electron beam between a dielectric material, disposed above the first conductor point, and the second conductor point through theporosity or the anomaly in the material; and measuring at least one of an electric discharge and a change in an electric field with a sensor, further comprising the steps of:

securing the material on the dielectric material as a partition in a capsule;

flushing a first side of the partition with an electrically charged conductive or neutral fluid;

introducing a cover gas from a second side of the partition; and the step of flowing the electron beam includes flowing the electron beam through the flow of the cover gas between a source of the electron beam and the porosity or the anomaly in the material.

23. An apparatus for the non-destructive testing and detecting of at least one of a porosity and an anomaly of a material, comprising:

means for generating a point-to-point effect including:

means for flowing an electron beam in an open atmosphere through a fluid cover gas between a first conductor point and a second conductor point through the porosity or the anomaly in the material, the material disposed on a conductive model, and the second conductor point being formed on the conductive model at the porosity or the anomaly, and focusing resistance means for controlling the beam size of the electron beam so as to prevent avalanche discharge; and sensor means for measuring at least one of an electric discharge and a change in an electric field, thereby to detect the porosity or anomaly.

24. The apparatus of claim 23 wherein the sensor means includes:

an anode for attracting a plurality of electrons;

a coil for detecting the plurality of electrons; and an ammeter for measuring a flow of current in the coil.

25. The apparatus of claim 23 comprising:

wherein the anomaly is one of a contaminant, a blister, a bubble, an uncatalyzed resin, an unblended resin, a low density material, a material having a weak molecular crosslinking strength, a high density material, an overlapping material, formulation defect and a stress fracture, and wherein there exists an inverse relationship between the change in the electric field and the size of the porosity or the anomaly of the material.

26. The apparatus of claim 23 wherein the conductive model is one of a mandrel, a plate, a roller, and a point.

27. The apparatus of claim 23 wherein the fluid cover gas is one of nitrogen, a noncombustible gas, a noble gas, and dehydrated air.

28. The apparatus of claim 25 further comprising an automatic positioning device for positioning one of the conductive model and the sensor.

29. The apparatus of claim 28 wherein the automatic positioning device is one of a servo motor, a stepper motor, and a programmable robot.

30. The apparatus of claim 23 further comprising:

a capsule in which the material is placed;

means for flushing the capsule with an electrically charged conductive or neutral fluid; and means for flowing the electron beam through a fluid cover gas.

31. The apparatus of claim 30 wherein the electrically charged conductive or neutral fluid is one of a noble gas, an alkaline gas, an acidic gas, a heated gas, and a conductive liquid.

32. The apparatus of claim 30 wherein the fluid cover gas is one of nitrogen, a noncombustible gas, a noble gas, and dehydrated air.

33. The apparatus of claim 30 further comprising automatic positioning means for positioning the sensor.

34. The apparatus of claim 33 wherein the automatic positioning means is one of a servo motor, a stepper motor, and a programmable positioning robot.

35. The apparatus of claim 23 further comprising:

means for flowing the electron beam between a dielectric material, disposed above the second conductor point, and the first conductor point through the porosity or the anomaly in the material.

36. The apparatus of claim 35 further comprising:

field strength attenuator means disposed around the second conductor point for decreasing a field intensity of the electron beam.

37. An apparatus for the non-destructive testing and measuring of at least one of a porosity and an anomaly of a material, comprising:

means for generating a point-to-point effect including means for flowing an electron beam between a first conductor point and a second conductor point through the porosity or the anomaly in the material, the material disposed on a conductive model, and the second conductor point being formed on the conductive model at the porosity or the anomaly;

means for flowing the electron beam between a dielectric material, disposed above the second conductor point, and the first conductor point through the porosity or the anomaly in the material; and sensor means for measuring at least one of an electric discharge and a change in an electric field, further comprising:

one of a dielectric screen and an anomaly-free dielectric film disposed between the material and the conductive model, the material being placed on the dielectric screen or the anomaly-free dielectric film, the dielectric material being the dielectric screen or the anomaly-free dielectric film;

means for introducing a first fluid cover gas between the material and the first conductor point; and means for flowing the electron beam through the first fluid cover gas.

38. The apparatus of claim 37 wherein the dielectric material is nylon.

39. The apparatus of claim 37 further comprising:

means for introducing a second fluid cover gas between a surface of the dielectric material and the second conductor point; and means for flowing the electron beam through the second fluid cover gas.

40. The apparatus of claim 39 wherein each one of the first fluid cover gas and second fluid cover gas is one of nitrogen, a noncombustible gas, a noble gas, and dehydrated air.

41. The apparatus of claim 37 wherein the dielectric material is positioned between the first conductor point and the second conductor point.

42. The apparatus of claim 41 further comprising:

a capsule in which the material, secured on the dielectric material, is placed; and means for flushing the capsule with an electrically charged conductive or neutral fluid.

43. The apparatus of claim 37 further comprising:

means for directing a draw of one of a vacuum and a partial vacuum from a surface of the dielectric material; and means for flowing the electron beam through the one of the vacuum and the partial vacuum.

44. The apparatus of claim 24 wherein the focusing resistance means has a resistance value between 1 kiloohm and 1000 teraohms.

45. The apparatus of claim 44 wherein the resistance value has a preferred range of 30 gigaohms to 90 gigaohms.

46. The method of claim 1 wherein the material is a dielectric bag having a conductive content.

47. The apparatus of claim 23 wherein the material is a dielectric bag having a conductive content.

48. The apparatus of claim 24 further comprising an electric field analyzer for measuring the change in the electric field.

49. A method for the non-destructive testing and measuring of the integrity of a material, comprising the steps of:

placing the material on one of a conductive plate, a roller, a mandrel, a dielectric screen and an anomaly-free dielectric film;

generating a point-to-point effect by flowing an electron beam through a fluid cover gas through at least one of a porosity and an anomaly in the material from the one of the conductive plate, the roller, the mandrel, the dielectric screen and the anomaly-free dielectric film to a conductor point;

resisting the flow of electrons to control the size of the electron beam sufficiently to prevent avalanche discharge;

measuring at least one of an electric discharge and a change in an electric field with a sensor; and measuring and analyzing at least one of a waveshape, a frequency and an amplitude change associated with the electric discharge or the change in the electric field with a signal analyzer.

50. An apparatus for the non-destructive testing and measuring of the integrity of a material, comprising:

one of a conductive plate, a roller, a mandrel, a dielectric screen and an anomaly-free dielectric film on which the material is placed;

means for generating a point-to-point effect including means for flowing an electron beam through a fluid cover gas from the one of the conductive plate, the roller, the mandrel, the dielectric screen and the anomaly-free dielectric film to a conductor point, and focusing resistance means for controlling the beam size of the electron beam;

sensor means for measuring at least one of an electric discharge and a change in an electric field; and signal analyzer means for measuring and analyzing a change in at least one of amplitude, frequency and waveshape of the electric discharge or the change in the electric field.

* * * * *